(12) United States Patent
Foulds et al.

(10) Patent No.: US 10,159,979 B2
(45) Date of Patent: Dec. 25, 2018

(54) MICROFLUIDIC DEVICE FOR HIGH-VOLUME PRODUCTION OF MONODISPERSE EMULSIONS

(71) Applicant: King Abdullah University of Science and Technology, Thuwal (SA)

(72) Inventors: Ian G. Foulds, Thuwal (SA); David Conchouso González, Thuwal (SA); David Castro, Thuwal (SA)

(73) Assignee: KING ABDULLAH UNIVERSITY OF SCIENCE AND TECHNOLOGY, Thuwal (SA)

(*) Notice: Subject to any disclaimer, the term of this patent is extended or adjusted under 35 U.S.C. 154(b) by 106 days.

(21) Appl. No.: 15/035,222

(22) PCT Filed: Nov. 11, 2014

(86) PCT No.: PCT/IB2014/003011
§ 371 (c)(1),
(2) Date: May 6, 2016

(87) PCT Pub. No.: WO2015/068045
PCT Pub. Date: May 14, 2015

(65) Prior Publication Data
US 2016/0271610 A1    Sep. 22, 2016

Related U.S. Application Data

(60) Provisional application No. 61/902,600, filed on Nov. 11, 2013.

(51) Int. Cl.
*B01L 3/00* (2006.01)
*B01F 3/08* (2006.01)
(Continued)

(52) U.S. Cl.
CPC ...... *B01L 3/502784* (2013.01); *B01F 3/0807* (2013.01); *B01F 3/0811* (2013.01);
(Continued)

(58) Field of Classification Search
CPC ......... B01L 2200/0673; B01L 2200/12; B01L 2300/0803; B01L 2300/0874;
(Continued)

(56) References Cited

U.S. PATENT DOCUMENTS 4,354,932 A * 10/1982 McNeil ................. B01D 15/14
138/41
4,537,217 A * 8/1985 Allen, Jr. ............... B01D 15/14
137/561 A (Continued)

FOREIGN PATENT DOCUMENTS

| CN | 102389730 A | 3/2012 |
|---|---|---|
| JP | 2011206878 | 10/2011 |

(Continued)

OTHER PUBLICATIONS

First Examination Report in related Saudi Arabian Application No. 516371090, dated Oct. 29, 2017 (References a-c were provided in an IDS on May 6, 2016).

(Continued)

*Primary Examiner* — Tony G Soohoo
(74) *Attorney, Agent, or Firm* — Patent Portfolio Builders, PLLC

(57) ABSTRACT

A high volume microfluidic system for producing emulsions includes a fluid distribution network to produce uniformly sized emulsions and encapsulates.

15 Claims, 23 Drawing Sheets

(51) Int. Cl.
*B01F 5/06* (2006.01)
*B01F 13/00* (2006.01)
*B01F 13/10* (2006.01)
*B01F 15/02* (2006.01)
*G01N 1/40* (2006.01)

(52) U.S. Cl.
CPC ........ *B01F 5/0601* (2013.01); *B01F 13/0062* (2013.01); *B01F 13/0066* (2013.01); *B01F 13/0069* (2013.01); *B01F 13/1022* (2013.01); *B01F 15/0264* (2013.01); *B01L 3/502707* (2013.01); *B01F 2003/0834* (2013.01); *B01F 2003/0842* (2013.01); *B01F 2003/0849* (2013.01); *B01L 2200/0673* (2013.01); *B01L 2200/12* (2013.01); *B01L 2300/0803* (2013.01); *B01L 2300/0874* (2013.01); *B01L 2300/0887* (2013.01); *B01L 2400/0487* (2013.01); *G01N 2001/4027* (2013.01)

(58) Field of Classification Search
CPC ..... B01L 2300/0887; B01L 2400/0487; B01L 3/502707; B01L 3/502784; B01F 13/0062; B01F 13/0066; B01F 13/0069; B01F 13/1022; B01F 15/0264; B01F 2003/0834; B01F 2003/0842; B01F 2003/0849; B01F 3/0807; B01F 3/0811; B01F 5/0601
See application file for complete search history.

(56) References Cited

U.S. PATENT DOCUMENTS

| | | | | | |
|---|---|---|---|---|---|
| 4,550,681 | A | * | 11/1985 | Zimmer | B05C 5/0254 101/120 |
| 4,999,102 | A | * | 3/1991 | Cox | B01D 15/14 137/561 A |
| 5,289,224 | A | * | 2/1994 | Devaney, Jr. | G03D 5/003 366/DIG. 3 |
| 5,304,487 | A | * | 4/1994 | Wilding | B01J 19/0093 210/500.26 |
| 5,354,460 | A | * | 10/1994 | Kearney | B01D 3/008 210/198.2 |
| 5,355,318 | A | * | 10/1994 | Dionnet | G06T 17/05 156/275.5 |
| 5,486,335 | A | * | 1/1996 | Wilding | B01F 15/0264 366/DIG. 3 |
| 5,938,333 | A | * | 8/1999 | Kearney | B01F 5/0601 138/42 |
| 6,333,019 | B1 | * | 12/2001 | Coppens | B01F 5/06 23/293 R |
| 6,616,327 | B1 | * | 9/2003 | Kearney | B01F 5/06 366/340 |
| 7,066,641 | B2 | * | 6/2006 | Honda | B01F 5/0604 366/340 |
| 8,511,889 | B2 | * | 8/2013 | Choikhet | B01F 5/064 138/40 |
| 9,340,802 | B2 | * | 5/2016 | Trevethick | C12M 29/18 |
| 2002/0080563 | A1 | * | 6/2002 | Pence | B01F 5/06 361/676 |
| 2002/0113095 | A1 | * | 8/2002 | Jeon | B01F 5/0601 222/424.5 |
| 2002/0187072 | A1 | * | 12/2002 | Karp | B01F 5/0471 422/400 |
| 2002/0196706 | A1 | * | 12/2002 | Kearney | B01F 5/06 366/336 |
| 2003/0039169 | A1 | | 2/2003 | Ehrfeld et al. | |
| 2003/0159742 | A1 | * | 8/2003 | Karp | B01F 5/0471 137/833 |
| 2004/0145967 | A1 | * | 7/2004 | Honda | B01F 5/0604 366/336 |
| 2007/0297285 | A1 | * | 12/2007 | Cross | B01D 3/008 366/340 |

FOREIGN PATENT DOCUMENTS

| | | |
|---|---|---|
| WO | 01/43857 A1 | 6/2001 |
| WO | 2008148200 A1 | 12/2008 |

OTHER PUBLICATIONS

International Search Report dated May 4, 2015, issued in International Application No. PCT/IB2014/003011.

Written Opinion of the International Searching Authority dated May 4, 2015, issued in International Application No. PCT/IB2014/003011.

Notification Concerning Transmittal of International Preliminary Report on Patentability (Chapter I of the Patent Cooperation Treaty) dated May 26, 2016, issued in International Application No. PCT/IB2014/003011.

Written Opinion of the Intellectual Property Office of Singapore in related SG Application No. 11201603654U, dated Feb. 22, 2017 (All citations previously provided, US 2003/00319169 cited herein as patent family member).

Office Action from the Chinese Patent Office in related CN Application No. 201480072879.9, dated Apr. 12, 2017 (Citations 2-5 previously provided).

\* cited by examiner

A

B

MICROFLUIDIC DEVICE FOR HIGH-VOLUME PRODUCTION OF MONODISPERSE EMULSIONS

CLAIM OF PRIORITY

This application claims the benefit under 35 USC 371 to International Application No. PCT/IB2014/003011, filed Nov. 11, 2014, which claims priority to U.S. Provisional Patent Application No. 61/902,600, filed Nov. 11, 2013, each of which is incorporated by reference in its entirety.

TECHNICAL FIELD

This invention relates to a device and method for producing monodisperse emulsions and a continuous post-processing technique.

BACKGROUND

Microfluidics has gained increasing interest, having the potential of being applied in areas such as lab-on-a-chip, fuel cells, diagnostic systems, microreactors, synthesis of materials and many others. Microfluidics also offers potential for producing uniformly sized emulsions and encapsulates that are of interest to businesses such as drug delivery and consumer goods. The creation of highly monodisperse emulsions can be very important for companies such as pharmaceutical, cosmetics, aggressive and fine chemicals, and food industries.

SUMMARY

A multi-layer microfluidic device for parallelization of microfluidic systems can include a distribution network including a plurality of channels to control the flow of a fluid, the distribution network being formed in at least two layers of plates or substrates to form a fractal pattern of fluid channels aligned between the layers by through-holes in each layer. The fractal pattern of fluid channels can run simultaneously. The parallelization allows the user to simultaneously run multiple microfluidic systems, which can produce microfluidic emulsions in large quantities.

The device can include inputs that are accessible from a surface of the device. The channels can be on a substrate or plate made of polymeric plastic material such as poly(methyl-methacrylate), stainless steel, ceramics, or glass or a combination thereof. The channels can be arranged in a pattern based on any number that follows the equation $p \times m \times 2^n$, where p is an integer representing the number of petals, m is an integer representing the number of identical generation layers and n is an integer representing the number of levels of the fractal branching. The distribution network can connect a stack of plates or substrates forming emulsion generation layers. The distribution network can include at least two distribution layers, each distribution layer including a fractal pattern of fluidic channels and through holes interconnecting them with the stack of emulsion generation layers. The device can include at least one inlet or input and at least 1 outlet or output to allow accessibility of immiscible liquids and exit of droplets. In certain embodiments, the device can include at least one inlet or input per immiscible fluid.

A method of forming an emulsion can include passing a fluid through a multi-layer device comprising at least two layers, wherein the two layers are connected by through-holes, wherein each layer includes a fractal pattern, and wherein each layer includes a distribution network connecting with channels of the device to control the flow of a fluid to an outlet that dispenses the emulsion. The emulsion can be monodisperse or polydisperse.

A method for post-processing an emulsion can include supplying a fluid to a processing zone having a curved surface such that the fluid forms a uniform and continuous layer free of side edges. The processing zone can include a tube having a curved surface. Alternatively, the processing zone can include an open rounded surface similar to a ball-fountain. The method can include aligning emulsion output around a tube having a curved surface or around the open rounded surface. The method can include thermally treating on the curved surface to form crystals and other monodisperse particles suitable for pharmaceutical, coating or other applications or UV treating on the curved surface to form crystals and other monodisperse particles.

In one aspect, multi-layer microfluidic device can include a distribution network connecting with a channel of the device to control the flow of a fluid, the distribution network including at least two plate or substrate layers, each layer including and engraved with a pattern of channels aligned between the plate or substrate layers through holes to allow combining of immiscible liquids and formation of uniform droplets. In the multi-layer device, fluid can flow from layer to layer in the device.

In certain embodiments, the device can include axisymmetric inputs that are accessible from a surface of the device. If more liquids are included the inputs can start from a point and then be directed to the middle for the initial distribution. The thickness of each layer can be less than 1 mm or more whereas, the channels can be formed on a substrate or plate can be made of polymeric material such as poly(methyl-methacrylate) or any other material such as a metal, for example, stainless steel, silicon, glass or ceramics or combination of any of the above.

In certain embodiments, the engraved pattern on the plate can result in low or high number of channels ranging from at least 2 channels and more following this equation at least $p \times m \times 2^n$ microfluidic droplet generators (MFDGs), where p is an integer representing the number of petals (explained below), m is an integer representing the number of identical generation layers and n is an integer representing the number of levels of the fractal branching, and thus $p \times 2^n$ is the number of generators per layer. For example, the device can include at least 128 channels, at least 256 channels, at least 512 channels, or at least 1024 channels.

The device can include multiple layers that distribute any number of immiscible fluids required by the chemistry of the process being used. Each layer can correspond to an individual fluid. In certain embodiments, the device can further include a water distribution layer. The device can include an oil-distribution layer. The device can include a cover layer.

In another aspect, a system for processing an emulsion can include a closed curved surface or an open rounded surface and at least one output supplying the emulsion as a layer on a surface of the closed curved surface. The system can include at least four outputs supplying the emulsion. The output can include a plurality of outputs aligned around the closed curved surface. The emulsion can wet the entire perimeter of a cross section of the closed curved surface to eliminate side edges with dry counterpart. Processing in this way allows microfluidic emulsions to be handled in large quantities, by a develop post-processing system that can handle the volume of product created by the parallelized system.

In certain embodiments, the system can be connected to a multi-layer microfluidic device comprising at least two layers, wherein the two layers are connected by through-holes, wherein each layer includes a fractal pattern, and wherein each layer includes a distribution network connecting with channels of the device to control the flow of a fluid. Each layer can include distribution channels and through holes.

In another aspect, a method for preparing an emulsion can include using a multi-layer microfluidic device comprising at least two layers wherein the two layers are connected by through-holes, wherein each layer includes a fractal pattern, and wherein each layer includes a distribution network and a plurality of channels of the device to control the flow of a fluid. At least one layer can include a rigid material.

In certain embodiments, the emulsions can be monodisperse. The production rate of the emulsions can be at least 300 mL/h.

In another aspect, a method for processing an emulsion can include supplying a fluid from a mixer or a source of emulsion to a processing zone having a curved surface such that the fluid forms a layer free of side edges of transition from a wetted surface to a dry surface. The processing zone can include a tube having a curved surface or an open rounded surface. The fluid can contact a wall of the surface to form a thin film. The fluid can wet the entire perimeter of the curved surface. The surface can collect and evenly distribute the output of an emulsion supply so that it can be continuously and uniformly processed. Examples of this process can include thermal or UV exposure treatment. In one embodiment, a circular cylinder can have its walls evenly coated with a thin layer of flowing emulsion that slides downwards and allows post-processing. In another embodiment, an open rounded surface can have its surface evenly coated with a thin layer of flowing emulsions. In certain embodiments, the open rounded surface can be an opened sphere. In certain other embodiments, the open rounded surface can be a rounded column.

In certain embodiments, the method can use at least four outputs to supply the fluid from the mixer to the processing zone. The method can include aligning emulsion output around a tube having a curved surface.

In certain embodiments, the method can include heating the curved surface. The method can include heating a layer of the fluid without an edge. The method can include exposing the processing zone to an ultraviolet light.

In one aspect, a multi-layer microfluidic device can include a distribution network connecting a stack of emulsion generation layers, wherein the distribution network can include at least two distribution layers, each distribution layer including a fractal pattern of fluidic channels and through holes interconnecting them with the stack of emulsion generation layers. The number of the generation layers can be an integer, for example, 1, 2, 3, 4, 5, 6, 7, 8, 9, or 10, more. The emulsion generation layers can be formed by a polar array of microfluidic droplet generators. The emulsion generation layers can include at least 128 generators, or at least 256 generators, or least 512 generators, or at least 1024 generators. Each generator can be a channel described above. Others configurations of the device can have different numbers of generators according to the number of petals and the number of generators per petal.

Other aspects, embodiments, and features will be apparent from the following description, the drawings, and the claims.

BRIEF DESCRIPTION OF THE DRAWINGS

FIG. 12A is a graph depicting the droplet size at different disperse phase flow rates. FIG. 12 B is a graph depicting the coefficient of variation as a function of flow rate per generation layer.

FIG. 19A is an SEM image of glycine spherical crystal agglomerates. FIG. 19B is a schematic depicting the crystallization sequence consist of rapid shrinkage of the droplet, nucleation, spherulitic crystal growth, and aging. FIG. 19C is an SEM image of glycine crystal agglomerates. FIG. 19D is an optical image of glycine spherical crystal agglomerates.

FIG. 20A is an annular distribution network. FIG. 20B is an annular distribution network combined with a tree-like structure. FIG. 20C is a fractal tree-like distribution network. In the insets blue represents the feed lines of the aqueous phase whereas orange denotes the path of the oil phase. For FIG. 20C, the aqueous and oil phases have the same paths but in different layers and are aligned to form petals.

DETAILED DESCRIPTION

Figure 1:
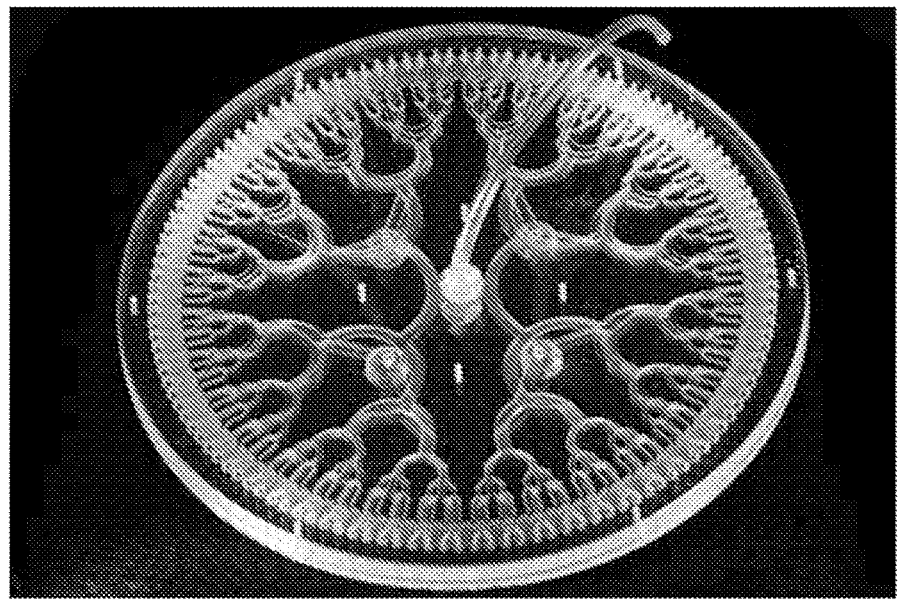
FIG. 1A shows a microfluidic chip with 256 channels, including 2-stacked layers of 128 channels each, fabricated in poly(methyl-methacrylate) ("PMMA").
FIG. 1B shows a lateral image of a device.
Figure 1:
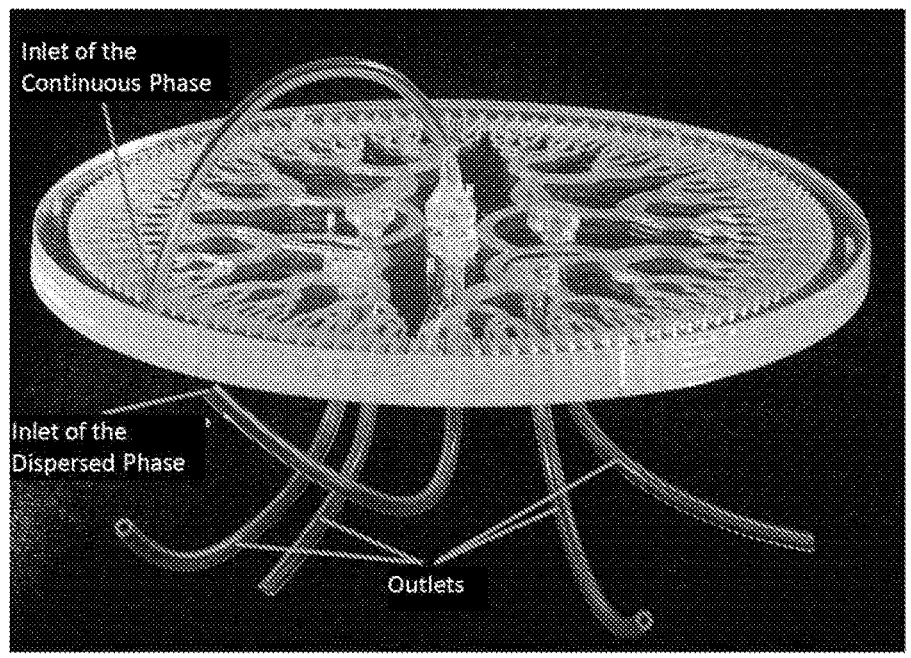

The development of droplet-based microfluidics in the past two decades has opened the doors for quick and continuous advancement in several research areas. Applications in fine chemistry, drug discovery, and biology have benefited from the miniaturization of their entire systems into nano to femtoliter size droplets. As a consequence of this size reduction, the surface area to volume ratio for a given system becomes larger, and surface related physics dominate over the volumetric phenomena. This technology has allowed new methods to accomplish experiments that were not possible on the macroscale. See, A. B. Theberge, F. Courtois, Y. Schaerli, M. Fischlechner, C. Abell, F. Hollfelder and W. T. S. Huck, *Small*, 2010, 49, 5846-5868, which is incorporated by reference in its entirety. For example, rapid heat transfer in droplets allows for precise temperature control in the synthesis of particles as well as on chip temperature cycling. See, E. Chan, A. Alivisatos and R. Mathies, *J. Am. Chem. Soc.*, 2005, 127, 13854-13861, S. Xu, Z. Nie, M. Seo, P. Lewis, E. Kumacheva, H. A. Stone, P. Garstecki, D. B. Weibel, I. Gitlin and G. M. Whitesides, Angew. Chem., 2005, 117, 734-738, and Y. Schaerli, R. C. Wootton, T. Robinson, V. Stein, C. Dunsby, M. A. A. Neil, P. M. W. French, A. J. deMello, C. Abell and F. Hollfelder, *Anal. Chem.*, 2009, 81, 302-306, each of which is incorporated by reference in its entirety. Other reaction parameters that can be controlled at the scale of a droplet include: quantity of reagents, mixing rate (either by diffusion or assisted by a microfluidic mixer), residence time, and other parameters related to the post-processing steps (e.g. UV exposure time, crystallization temperature etc.). See, D. J. Han, J. H. Jung, J. S. Choi, Y. T. Kim and T. S. Seo, *Lab Chip*, 2013, 13, 4006-4010, G. T. Vladisavljević, N. Khalid, M. A. Neves, T. Kuroiwa, M. Nakajima, K. Uemura, S. Ichikawa and I. Kobayashi, Adv. Drug Delivery Rev., 2013, 65, 1626-1663, and E. Chan, A. Alivisatos and R. Mathies, *J. Am. Chem. Soc.*, 2005, 127, 13854-13861, each of which is incorporated by reference in its entirety.

The inherent low consumption of reagents and the enhanced control over the droplet environment conditions maintain the promise to enable high-throughput screening of chemical and biological libraries. For example, droplet-based microfluidics has been used for studies in molecular analysis, and single cell studies where valuable reagents can be expend in smaller volumes. See, J. Hong, J. B. Edel and A. J. deMello, *Drug Discovery Today*, 2009, 14, 134-146, S.-Y. Teh, R. Lin, L.-H. Hung and A. P. Lee, *Lab chip*, 2008, 8, 198, and M. T. Guo, A. Rotem, J. A. Heyman and D. A. Weitz, *Lab Chip*, 2012, 12, 2146-2155, each of which is incorporated by reference in its entirety. Since reactions are confined in minute quantities, reactive reagents and products can also be handled with low risk, when safety is of concern.

Thanks to all of the benefits that droplet microfluidics offers, studies of complex reaction kinetics and synthesis of engineered particles have been feasible in various fields. Examples of particles designed and synthesized by this technology include: polymer particles, 17,18 microcapsules, nanoparticles, quantum dots, photonic beads, etc. See, M. Seo, Z. Nie, S. Xu, M. Mok, P. C. Lewis, R. Graham and E. Kumacheva, Langmuir, 2005, 21, 11614-11622, J. I. Park, A. Saffari, S. Kumar, A. Günther and E. Kumacheva, *Annu. Rev. Mater. Res.*, 2010, 40, 415-443, R. K. Shah, H. C. Shum, A. C. Rowat, D. Lee, J. Agresti, A. S. Utada, L.-Y. Chu, J.-W. Kim, A. Fernandez-Nieves, C. J. Martinez and D. A. Weitz, Mater. *Today*, 2008, 11, 18-27, W. J. Duncanson, T. Lin, A. R. Abate, S. Seiffert, R. K. Shah and D. A. Weitz, *Lab Chip*, 2012, 12, 2135-2145, K.-S. Huang, K. Lu, C.-S. Yeh, S.-R. Chung, C.-H. Lin, C.-H. Yang and Y.-S. Dong, *J. Controlled Release*, 2009, 137, 15-19, C. H. Yang, K. S. Huang, Y. S. Lin, K. Lu, C. C. Tzeng, E. C. Wang, C. H. Lin, W. Y. Hsu and J. Y. Chang, *Lab Chip*, 2009, 9, 961-965, S. A. Khan and S. Duraiswamy, Lab Chip, 2012, 12, 1807-1812, S. Duraiswamy and S. A. Khan, *Small*, 2009, 5, 2828-2834, A. M. Nightingale and J. C. de Mello, *Chem Phys Chem*, 2009, 10, 2612-2614, and Y. Zhao, X. Zhao, J. Hu, M. Xu, W. Zhao, L. Sun, C. Zhu, H. Xu and Z. Gu, *Adv. Mater.*, 2008, 21, 569-572, each of which is incorporated by reference in its entirety.

To generate these microreactors a Microfluidic Droplet Generator (MFDG) is used. The different types of MFDGs and their characteristics are summarized elsewhere. See, for example, C.-X. Zhao, Adv. Drug Delivery Rev., 2013, 65, 1420-1446, R. K. Shah, H. C. Shum, A. C. Rowat, D. Lee, J. Agresti, A. S. Utada, L.-Y. Chu, J.-W. Kim, A. Fernandez-Nieves, C. J. Martinez and D. A. Weitz, Mater. *Today*, 2008, 11, 18-27, J.-T. Wang, J. Wang and J.-J. Han, Small, 2011, 7, 1728-1754, and G. T. Vladisavljević, I. Kobayashi and M. Nakajima, Microfluid. *Nanofluid.*, 2012, 13, 151-178, each of which is incorporated by reference in its entirety. A typical MFDG is a set of microchannels that bring two immiscible fluids together to a point. In this junction the interaction between the interfacial tension and the viscous forces of both liquids leads to droplet formation.

The distribution of the output of these devices can be measured by their coefficient of variation (Cv), which is defined as the ratio between a sample's standard deviation and mean diameter. When the distribution is narrow enough (Cv≤5%), the emulsion is said to be monodisperse. See, A. Jillavenkatesa, S. J. Dapkunas and L.-S. H. Lum, *Particle Size Characterization*, Washington, 2001, which is incorporated by reference in its entirety. Even though numerous advancements in droplet microfluidics have been demonstrated, the low volume throughput associated with these studies has hindered their adoption in the industry. A typical production rate for a single MFDG is approximately 1-10 mL/h of droplets whereas industrial applications usually demand production rates several orders of magnitude higher. See, T. Nisisako, T. Ando and T. Hatsuzawa, *Lab Chip*, 2012, 12, 3426-3435, which is incorporated by reference in its entirety. This drawback has made droplet microfluidics technology only attractive for high added value industries such as pharmaceutical, food, fine chemical, and cosmetics. See, C. Haber, *Lab Chip*, 2006, 6, 1118-1121, G. M. Whitesides, Nature, 2006, 442, 368-373, G. Muschiolik, *Curr. Opin. Colloid Interface Sci.*, 2007, 12, 213-220, and O. Skurtys and J. M. Aguilera, *Food Biophysics*, 2007, 3, 1-15, each of which is incorporated by reference in its entirety.

A possible solution to increase the total production of droplets and droplet-based microfluidic applications is parallelization, which consists of numbering up the individual MFDGs working simultaneously with shared inputs. Currently in the industry, there are several methods of droplet generation in the form of emulsions. See, M. F. Edwards, N. Hamby and A. W. Nienow, *Mixing in the Process Industries*, Butterworth-Heinemann, 2nd edn. 1992, and P. Walstra, *Chem. Eng. Sci.*, 1993, 48, 333-349, each of which is incorporated by reference in its entirety. Conventional emulsification techniques use continuous high-shear mixing of two immiscible phases to generate batch production of emulsions in a container. Examples of these methods are: high-speed blenders, colloid mills, high-pressure homogenizers, and ultrasonic homogenizers. See, D. J. McClements, *Food Emulsions: Principles, Practice, and Techniques*, CRC Press LLC, 1999, and S. M. Joscelyne and G. Trägårdh, *J. Membr. Sci.*, 2000, 169, 107-117, each of which is incorporated by reference in its entirety. They typically produce droplets in the range of 0.1 to 100 μm diameter, at wide size distributions (Cv ~30%) and with production rates in the order of 100-20,000 L/h.

Membrane emulsification is a second type of emulsification technique, in which the disperse phase is pressure driven through a controlled-size porous membrane into the continuous phase. See, R. A. Williams, S. J. Peng, D. A. Wheeler, N. C. Morley, D. Taylor, M. Whalley and D. W. Houldsworth, *Chem. Eng. Res. Des.*, 1998, 76, 902-910, and T. Nakashima, M. Shimizu and M. Kukizaki, *Adv. Drug Delivery Rev.*, 2000, 45, 47-56, each of which is incorporated by reference in its entirety. The size and size distribution of the droplets strongly depend on the membrane's pore size. Typically, the droplet size range is in between 0.1 to 10 μm diameter, with coefficients of variation of 10-20% and production rates of 15 to 300 L/h. A similar method is the so-called microchannel emulsification, which utilizes a substrate with microfabricated channels or slits instead of pores in a membrane. See, I. Kobayashi, Y. Wada, K. Uemura and M. Nakajima, Microfluid. *Nanofluid.*, 2010, 8, 255-262, I. Kobayashi, M. A. Neves, Y. Wada, K. Uemura and M. Nakajima, *Green Processes Synth.*, 2012, 1, 353-362, each of which is incorporated by reference in its entirety. This technology allows a much narrower size distribution (Cv<5%), but at lower production volumes. An example of this, reporting a production rate of 1.4 L/h, is the work of Kobayashi et al. Microholes were deep reactive ion etched on a silicon on insulator wafer. The microfabricated structure was then placed in between two pressurized chambers and the disperse phase flows through the microholes into the continuous phase, as compared to the case of membrane emulsification.

TABLE 1

Summary of microfluidic emulsion generator technologies

| Type and number of parallel generators | Distribution scheme | 3D Integration | Substrate & Young's modulus (GPa) | Production volume (mL/h) | Droplet diameter (μm) & Cv | Reference* |
|---|---|---|---|---|---|---|
| Flow focusing (512) | Tree (petal) (symmetric inputs) | Yes | PMMA 1.8-3.2 | 1000 | 100 to 200 6% | This work |
| Flow focusing (144) | Coaxial annular (asymmetric inputs) | No | Glass 50-90 | 180 | 90.7 2.2% | Nisisako |
| Flow focusing (16) | Tree | No | PDMS $0.75 \times 10^{-3}$ | 50 | 141 3.7% | Li |
| Flow focusing (15) | Ladder (asymmetric inputs) | Yes (Challenging alignment) | PDMS $0.75 \times 10^{-3}$ | 40 | 150 6% | Romanowsky |
| Flow focusing (512) | Ladder (asymmetric inputs) | No | PDMS $0.75 \times 10^{-3}$ | 8 | 86.1 9% | Muluneh |
| Flow focusing (180) | Ladder (asymmetric inputs) | No | PMMA-SU8 $1.8^{-5}$ | 2.5 | 21 5% | Tetradis-Meris |
| Flow focusing (96) | Tree (independent connections) | No | Glass 50-90 | 10 | 162 3.8% | Zeng |
| T-junction (16) | Ladder (asymmetric inputs) | No | Polycarbonate 2-2.4 | 25 | 200 to 600 N/A | Guzowski |
| Gradient of confinement (256) | Annular (asymmetric inputs) | No | PDMS $0.75 \times 10^{-3}$ | 3.6 | 36 to 41 3% | Dangla-PNAS |
| Gradient of confinement (339) | Annular (symmetric input) | No | PDMS $0.75 \times 10^{-3}$ | 60 | 80 1% | Dangla-Freiburg |

*See, T. Nisisako, T. Ando and T. Hatsuzawa, *Lab Chip*, 2012, 12, 3426-3435 ("Nisisako"), W. Li, J. Greener, D. Voicu and E. Kumacheva, *Lab Chip*, 2009, 9, 2715 ("Li"), M. B. Romanowsky, A. R. Abate, A. Rotem, C. Holtze and D. A. Weitz, *Lab Chip*, 2012, 12, 802 ("Romanowsky"), M. Muluneh and D. Issadore, *Lab Chip*, 2013, 13, 4750-4754 ("Muluneh"), G. Tetradis-Meris, D. Rossetti, C. Pulido de Torres, R. Cao, G. Lian and R. Janes, *Ind. Eng. Chem. Res.*, 2009, 48, 8881-8889 ("Tetradis-Meris"), Y. Zeng, R. Novak, J. Shuga, M. T. Smith and R. A. Mathies, Anal. Chem., 2010, 82, 3183-3190, ("Zeng"), J. Guzowski, P. M. Korczyk, S. Jakiela and P. Garstecki, *Lab Chip*, 2011, 11, 3593-3595("Guzowski"), R. Dangla, S. C. Kayi and C. N. Baroud, *Proc. Natl. Acad. Sci. U.S.A.*, 2013, 110, 853-858("Dangla-PNAS"), R. Dangla and C. N. Baroud, Production of Monodisperse Bulk Emulsions in a Beaker Using a Novel Microfluidic Device, Freiburg, 2013, pp. 83-85 ("Dangla-Freiburg"), each of which is incorporated by reference in its entirety.

A summary of the microfluidic emulsion generator technologies is found in Table 1. Dangla et al. recently introduced another variation of the microchannel emulsification systems to create monodisperse emulsions. In this work, droplet formation is mediated by confinement gradients in microchannels. These channels, on one end, have tapered walls to create droplet production nozzles with small inclination angles. In this system, droplet formation is relatively slow since it does not depend on the fluid flows but on the geometry of these nozzles (confinement). Even though 256 nozzles were parallelized, the maximum production rate was about ~3.6 mL/h.

Although some of these methods produce monodisperse droplets, they cannot fully incorporate all of the advantages of droplet microfluidics. A parallel MFDG emulsification device retains control over the droplets at all time (i.e. inside a microchannel) and preserves the other advantages given by a single MFDG system. Since parallel systems connect several MFDGs in a device, complex fluid mechanic couplings occur between adjacent devices. Crosstalk and many other factors can unbalance the system and produce a polydisperse output. Some of these sources of variation include: hydraulic resistance variations depending on the number of droplets a channel contains, pressure variations inherent in droplet formation (pressure changes during droplet pinch off), fabrication differences among the channels, irregularities in pumping, nonuniform loading, air bubbles and debris trapped in a particular channel, etc. See, W. Li, J. Greener, D. Voicu and E. Kumacheva, *Lab Chip,* 2009, 9, 2715, P. Parthiban and S. A. Khan, Biomicrofluidics, 2013, 7, 044123, P. Parthiban and S. A. Khan, *Lab Chip,* 2012, 12, 582-588, C. N. Baroud, F. Gallaire and R. Dangla, *Lab Chip,* 2010, 10, 2032-2045, G. Tetradis-Meris, D. Rossetti, C. Pulido de Tones, R. Cao, G. Lian and R. Janes, Ind. Eng. Chem. Res., 2009, 48, 8881-8889, and T. Ward, M. Faivre, M. Abkarian and H. A. Stone, *Electrophoresis,* 2005, 26, 3716-3724, each of which is incorporated by reference in its entirety.

A parallel MFDG emulsification device that has demonstrated high-volume production of monodisperse O/W emulsions (Cv=2.2%) in a microfluidic chip was proposed by Nisisako et al. See, T. Nisisako, T. Ando and T. Hatsuzawa, *Lab chip,* 2012, 12, 3426-3435, which is incorporated by reference in its entirety. This system produces emulsions at a maximum flow rate of 180 mL/h, for an array of 144 MFDGs working together. The chip was manufactured on a synthetic silica glass using photolithography and deep reactive ion etching. This fabrication process manufactures only one layer of generators and requires the use of an externally fabricated hydraulic manifold that is mechanically machined out of blocks of stainless steel. Although the annular manifold represents a solution to decouple parallel MFDGs, it limits the degree of scalability. The assembly of N+1 cylindrical blocks is required to be able to connect N coaxial annular channels, thus constraining this system to a relatively low number of annular channels feeding only one layer of generators. Moreover, this annular distribution network is fed laterally and due to the asymmetric connection between each annular channel and the piping, there are flow variations across the device (i.e. there are MFDGs closer to the connections).

Soft lithography has also been used to fabricate parallel MFDG emulsification devices using polydimethylsiloxane (PDMS). See, X.-H. Ji, N.-G. Zhang, W. Cheng, F. Guo, W. Liu, S.-S. Guo, Z.-K. He and X.-Z. Zhao, *J. Mater. Chem.,* 2011, 21, 13380-13387, and M. B. Romanowsky, A. R. Abate, A. Rotem, C. Holtze and D. A. Weitz, *Lab Chip,* 2012, 12, 802, each of which is incorporated by reference in its entirety. This fabrication technique also requires the use of a clean room facility to create high-aspect ratio master molds therefore its cost is still high. Using this fabrication method, Li et al. fabricated a multiple modular microfluidic device for the UV synthesis of polymeric particles at a production rate of 50 g/h. See, W. Li, J. Greener, D. Voicu and E. Kumacheva, *Lab Chip,* 2009, 9, 2715, which is incorporated by reference in its entirety. In this work, eight individual modules of 16 channels each were operated in parallel. These modules are independent chips that require a large amount of external connections and tubing, which limit higher scale parallelization.

In general, previous parallelization studies have mainly tried to explore only a second dimension for array expansion. However, if true parallelization is desired three-dimensional expansion has to be studied as well. A three-dimensional parallelization has been demonstrated in PDMS, however only 15 MFDGs in a stack of three layers were demonstrated, and due to their fabrication process, scaling up the number of MFDGs is challenging for the following reasons: the interconnecting through-holes between the stacking layers were manually made with a hole-puncher (i.e. process susceptible to error), and reproducible alignment in rubber-like materials such as PDMS is difficult to achieve. There are other types of technologies dealing with gas-liquid microreactors that have been parallelized in the past. For example, a multi-layer distribution device producing gas-liquid segmented flows in triangular channels was demonstrated using silicon. N. de Mas, A. Günther, T. Kraus, M. A. Schmidt and K. F. Jensen, *Ind. Eng. Chem. Res.,* 2005, 44, 8997-9013, which is incorporated by reference in its entirety. Similarly, production volumes for gas-liquid systems with modular flow distribution 58 have achieved flow rates as high as 9 L/h for devices operating at the Taylor flow regime and generating liquid segments with volumes in the range of 1.5-4.5 µL.

Microfluidic droplet generators ("MFDGs") can be used as manufacturing devices for monodisperse single and compound emulsions with controlled sizes and internal compositions. Emulsion drops can be used as versatile templates to engineer various particles having certain properties. For practical use in industry, however, MFDGs are limited by its throughput. The typical production of a microfluidic droplet generator is in the order of 10 g/h or less 100 kg/year while industry requirements are typically in the order of several tons a year. There has been an interest from many companies to develop a microfluidic solution that can increase the total production of emulsions to an industrially relevant scale. To have large scale production, it is important to increase the throughput by parallel numbering-up design of the MFDGs without increasing the number of hydraulic pumps and specialized equipment.

Disclosed herein are the design, fabrication and characterization of stackable microfluidic emulsion generators with coefficients of variation as low as ~6%. A multi-layer microfluidic parallelization chip for mass production of single emulsions can include another dimension for massive parallelization and the full integration of the distribution network within the chip, which is inherently scalable to even higher volumes. This device shows the highest throughput reported in the literature for a microfluidic device with simultaneous operation of liquid-liquid droplet generators. Production rates as high as 1 L/h of the disperse phase can be generated in devices containing four generation layers with 128 generators each, organized in a circular array. A minimum in dispersity for these particular devices occurred at 120 mL/h per layer. These layers can be interconnected via through-holes and fed with designated fractal distribution networks. The proposed layers can be milled on poly (methylmethacrylate) (PMMA) sheets and the stack can be thermo-compression bonded to create a multi-layer device with a high density of generators and an integrated distribution network. The effect of stacking multiple layers shows that fabrication accuracy has a greater impact on the dispersity of the emulsion than the addition of more layers to the stack.

A multilayer microfluidic device that simultaneously runs parallel units of microfluidic droplet generation by stacking layers of fluid distribution and layers of droplet generation. The different layers forming the stack can be aligned with each other using through-holes and a mechanical constriction. These layers can be formed by engraving microfluidic channels on substrates. The device can include an integrated distribution network in charge of feeding uniformly every parallel unit of droplet generation with fluids. The channels comprising the distribution network can be arranged using a fractal pattern which in turn can be organized in functional subunits which is called petals.

The fabrication process can be easily implemented in any high precision CNC milling machine and does not require the use of a clean room facility. This process is low-cost and enables the rapid prototyping of multi-layer microfluidic devices. Another advantage of this fabrication method is the greater stiffness of poly(methylmethacrylate) (PMMA) as compared to elastomers like PDMS. The rigid walls of these chips minimize the hydraulic capacitance of the microchannels and improve the transient response to flow changes.

This device can withstand pressures as high as 7.5 bar. Reproducible alignment was also achieved accurately (<5 µm) using metal pins and through-holes. In certain embodiments, a distribution network can be fully integrated within the microfluidic chip. In certain other embodiments, different types of distribution networks can be used in parallelization devices; tree-like, ladder-like in the coaxial annular configuration, or a combination of both. A fractal tree-like distribution network can minimize coupling. Groups of MFDGs can be organized in internally independent groups (petals), and neighboring MFDGs were disconnected at the lowest hierarchical level (i.e. the MFDG junction).

The effect on droplet size distribution of adding additional emulsion generation layers to the stack is disclosed for devices at different total flow rates. The dispersity did not show a direct correlation with the increase of the number of layers in the stack (e.g. 1-4 generation layers). However, since both phases are passed through the same distribution network and connected through-holes, an increase in the manifold resistance is expected for larger flow rates when more layers are stacked. An advantage of the tree-like distribution network is the fact that all individual MFDGs in a layer receive the same pressure drop from the fluidic inputs, so generation conditions are uniform across the device. Using thinner material sheets or larger diameter through-holes can minimize differences in pressure drops between generation layers.

In these devices, the fabrication variability of the milling process can contribute the most to the dispersity of the droplet size distribution and a more accurate patterning technique can significantly improve the emulsion dispersity. The centralized tree-like fractal distribution network showed the best results towards improving the droplet generation process because its configuration facilitates a uniform loading of both phases and bubble-free steady state performance. Furthermore, decoupling of groups of MFDGs for the rest of the device was demonstrated by arranging them in a petal-like structure. A double-layer parallelization chip with 256 channels and four petals was tested when one or more composing petals were deactivated. The droplet size and coefficient of variation for an operational section retained similar values when MFDGs were operated at equivalent flow rates.

Particle crystallization is presented as a pharmaceutical application that can be benefited from these parallel MFDG devices. Glycine spherical agglomerates can be successfully produced from the emulsion generated by these microfluidic devices. This example shows that the device can greatly facilitate the translation of methods such as active pharmaceutical ingredients ('API's) to industrially relevant scales of production by providing controlled microfluidic emulsification at liter-per-hour throughput—a crucial requirement in eventual scale-up processes. A straightforward combination of this emulsion generator in conjunction with high-throughput film evaporation can translate to industrial application.

Multi-Layer Microfluidic Device

High-volume parallelization of MFDG can be prepared. See, for example, T. Nisisako et al., *Lab on a chip*, pp. 3426-3435, June 2012, which is incorporated by reference in its entirety. However, Nisisako produces only one layer and requires the use of an externally fabricated distribution network, which limits the degree of scalability and the flow distribution over the MFDG, due to the asymmetric connection between each annular channel and the piping. A distribution network can include a set of distribution channels engraved in the distribution layers, and by the through-holes that connect the layers with each other.

Using a different method, a distribution network can be integrated within the design stage and is fabricated monolithically with the chip. In addition, thin layers (1 mm) can be used to keep the system compact and the distribution network lines can be produced on a single layer in order to maintain an even distribution of flow across the disk. The integration of the distribution network within a chip with axisymmetric inputs centered at the disk can produce an even loading of the liquid phases and can avoid trapping of air bubbles in the feed lines. This advantage contributes to the stability of the chip by reducing the flow variations in the diverse channels. Axisymmetric inputs can be accessible from a surface of the device. With this method, a multi-layer microfluidic device can include at least two layers, wherein at least one layer includes a rigid polymer, wherein the two layers are connected by through-holes, wherein each layer includes a fractal pattern, and wherein each layer includes a distribution network connecting with a channel of the device to control the flow of a fluid. The two layers can be parallel.

A multi-layer microfluidic device can be designed and fabricated for mass production of monodisperse single emulsions, producing droplets at the highest rate reported for a single chip (300 mL/h). The size of the droplets can depend on the size of the channels, the flow rates and the properties of the liquids. For example, using water and dodecane, a mean diameter of 175 µm (Cv=0.12) can be obtained. In another example, a mean droplet diameter of 225 µm and (Cv=0.09) can be obtained. FIG. 1A shows a microfluidic chip (110 mm diameter) with 256 channels, including 2-stacked layers of 128 channels each, fabricated in poly (methyl-methacrylate) (PMMA), where distribution networks and distribution network are also integrated on the device. FIG. 1B shows an example design of the layers that form a device for 2 fluids, with 2 distribution networks for oil and water supplies and 2 droplet generation layers. Parallelization of 256 cross-junction microfluidic droplet generators (MFDG) can be prepared and arranged in two layers using a low-cost process that integrates the distribution network within the chip. This design and fabrication method is flexible, allowing systems producing emulsions with tailored mean diameter and greater throughput than other methods.

The channels can have different geometries, and the geometries can affect droplet formation. The wide and shallow rectangular channel cross-section geometry (for example, rectangular 285×61 μm) is preferable over the other geometries (i.e. narrower rectangular and trapezoidal geometries) since it showed the lowest variability in droplet size with changing water/oil flow rate ratio. This trend was present in studies performed at different total flow rates, making the shallow rectangular geometry the most adequate for parallelization. At high total flows (i.e. 300 μl/min), larger capillary number, this behavior is more pronounced than at low flows (i.e. 30 μl/min). This behavior can be due to the reduced influence of the sidewalls in the generator.

Figure 2:
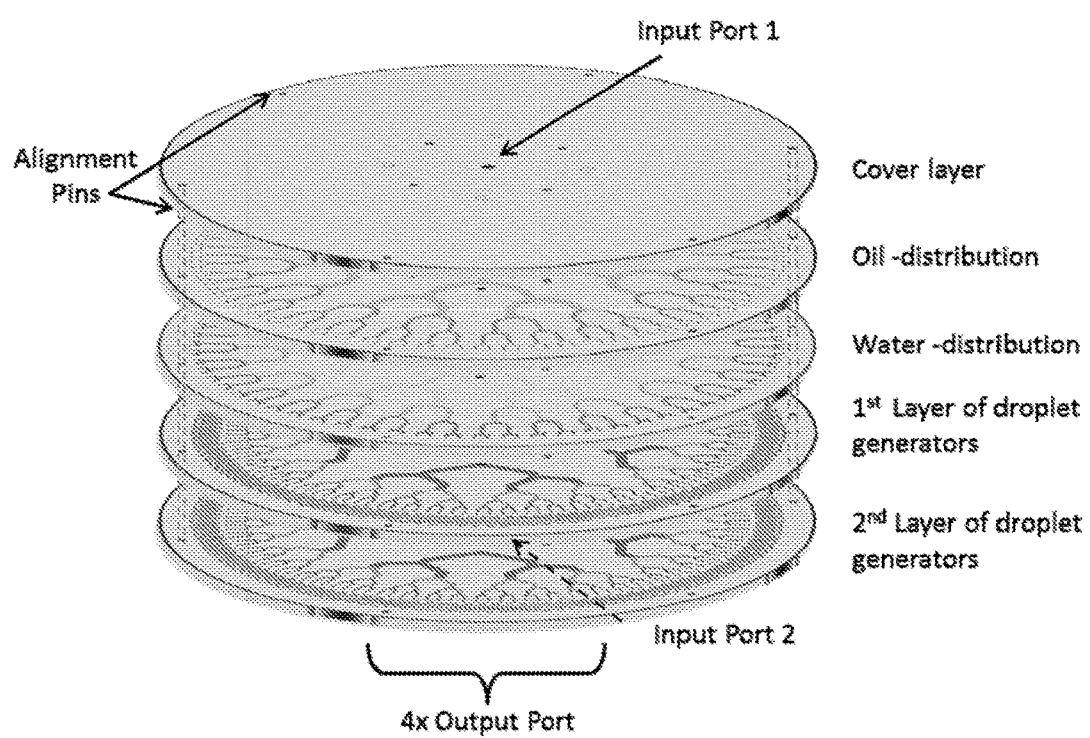
FIG. 2 shows an example design of the layers that form a device for two fluids, with two distribution networks for oil and water supplies and two droplet generation layers.

FIG. 2 shows an example design of the layers that form a device for 2 fluids, with 2 distribution networks for oil and water supplies and 2 droplet generation layers, including a stack of five layers. The bottom layers each contain 128 MFDG each, that are connected with through holes. Oil phase is added on the top while the water phase is input from the bottom. Both are centered to provide even distribution. More layers can be incorporated to stack a larger number of microfluidic droplet generators, offering a high degree of design flexibility. A system can have MFDG in an amount of any multiple of a fractalized pattern. For example, it can have 128, 256, 512, or 1024 MFDG, or any multiple of 128 MFDG. The bottom layers can contain an array of 128 channels each, which are interconnected by through-holes. On top of the stacked MFDG layers, another two layers of fractal distribution networks can be overlaid (one for each phase).

By integrating these networks and through-holes connecting the MFDG, a three-dimensional parallelization and integration of the distribution network within the chip can be prepared. An example of MFDG has been reported. See, for example, E. Chan et al., *J Am Chern Soc*, vol. 127, no. 40, pp. 13854-13861, 2005, which is incorporated by reference in its entirety.

When used to prepare a microfluidic device, examples of materials are poly(methyl methacrylate) (PMMA), cyclic olefin copolymer (COC), cyclic olefin polymer (COP), polycarbonate (PC), polyethylene terephthalate (PET), polydimethylsiloxane (PDMS), glass or silicon. In certain embodiments, a rigid component can have advantages for stack alignment, transient response and stability of the system. PMMA stiffness is in the order of 1.8-3.2 GPa, whereas COC (2.6-3.2 GPa), glass (50-90 GPa) and silicon (130-185 GPa) so devices that are made out of them can resist greater force/pressure before experiencing elastic deformation than devices made out of rubberlike materials whose Young's modulus is in the order of hundreds of Kilo-Pascal (i.e. PDMS Young's modulus is 360 to 870 KPa). See Table 2.

TABLE 2

Materials and Young's Modulus

| Rigid Materials | Young's Modulus |
| --- | --- |
| Poly(methyl methacrylate) (PMMA) | 1.8-3.2 GPa |
| Cyclic Olefin Copolymer (COC) | 2.6-3.2 GPa |
| Cyclic Olefin Polymer (COP) | 1.7-3.0 GPa |
| Polycarbonate (PC) | 2.0-2.4 GPa |
| Polyethylene terephthalate (PET) | 2.8-3.1 GPa |
| Off-Stoichiometry Thiol-Ene (OSTE) | 0.25-2.0 GPa |
| Glass | 50-90 GPa |
| Silicon | 130-185 GPa |

For example, soft-lithography can be used to fabricate high-throughput polydimethylsiloxane (PDMS) chips. See, for example, M. B. Romanowsky et al., *Lab on a Chip*, vol. 12, no. 4, p. 802, 2012; W. Li, et al., *Lab on a Chip*, vol. 9, no. 18, p. 2715, 2009, each of which is incorporated by reference in its entirety. This fabrication technique requires the use of a cleanroom facility to create high-aspect ratio master molds and therefore the fabrication cost is increased. Reproducible alignment in rubber-like materials such as PDMS can be more difficult to achieve than in rigid materials like PMMA in which pins and through-holes can be used to align (<5 μm).

PMMA's greater stiffness also minimizes the hydraulic capacitance and improves the transient response. Another important advantage of PMMA, COC, glass or silicon over PDMS is their low adsorption and absorption to chemicals and their low gas permeability. PMMA-SU8 substrate can be used to create a high throughput microfluidic device. See, for example, G. Tetradis-Meris et al., *Ind. Eng. Chern. Res.*, vol. 48, no. 19, pp. 8881-8889, October 2009, which is incorporated by reference in its entirety. Tetradis-Meris also reported that ladder-type layout was preferred to the tree-type arrangement with regard to liquid distribution from a distribution network into the parallelized device network. Id. However, the result is opposite for a multi-layer microfluidic device that includes at least two layers, wherein at least one layer includes a rigid polymer, wherein the two layers are connected by through-holes, wherein each layer includes a fractal pattern, and wherein each layer includes a distribution network connecting with a channel of the device to control the flow of a fluid.

A fractal pattern includes a fractal geometry, which has a particular type of structure that builds upon itself. A fractal pattern can include generations of progressively increasing or decreasing scale. The density of the fractal pattern increases with each repeating level. A multi-layer microfluidic device can have a fractal pattern with high density. The fractal pattern can include at least 128 channels, at least 256 channels, at least 512 channels, or at least 1024 channels.

Figure 3:
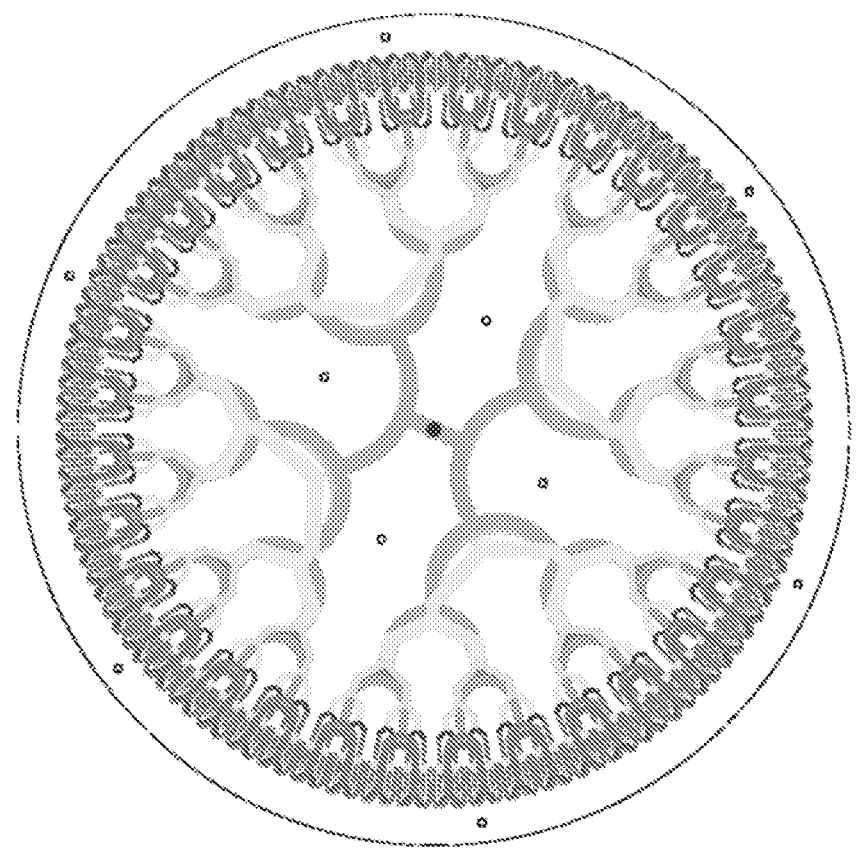
FIG. 3 shows an assembled stack.
Figure 4:
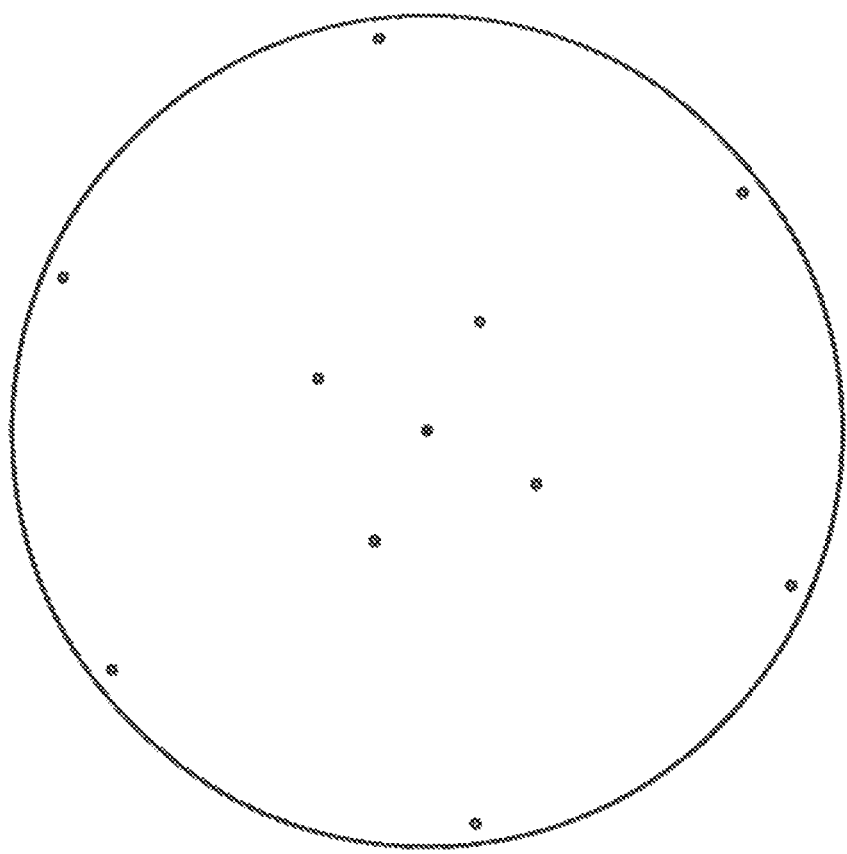
FIG. 4 shows a cap layer or a top layer.
Figure 5:
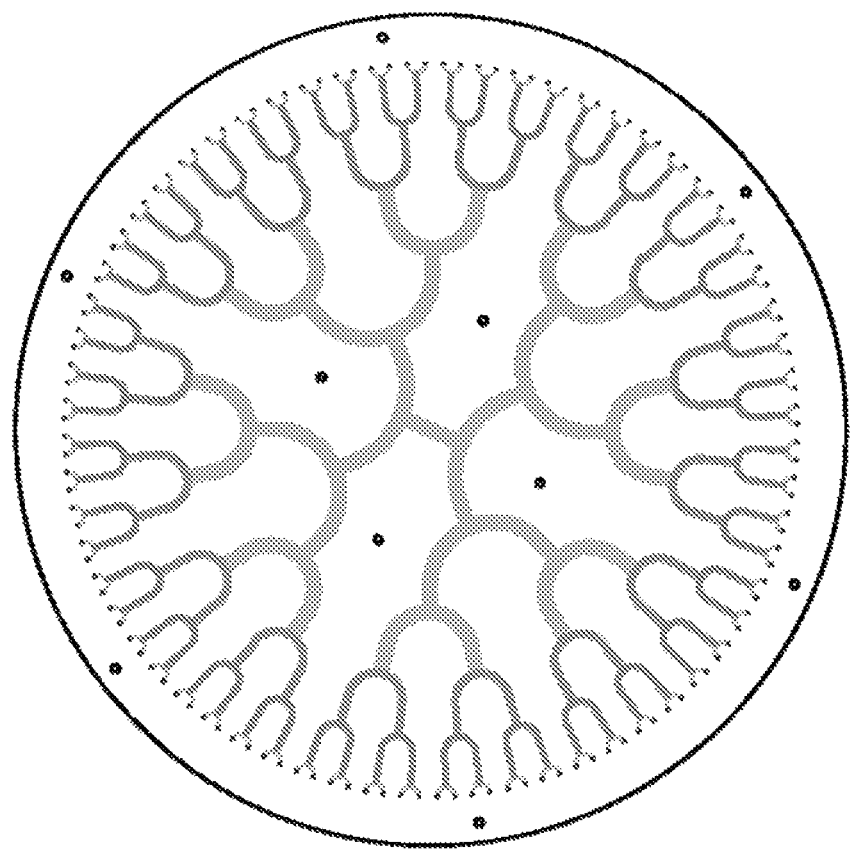
FIG. 5 shows continuous phase distribution network and distribution network.
Figure 6:
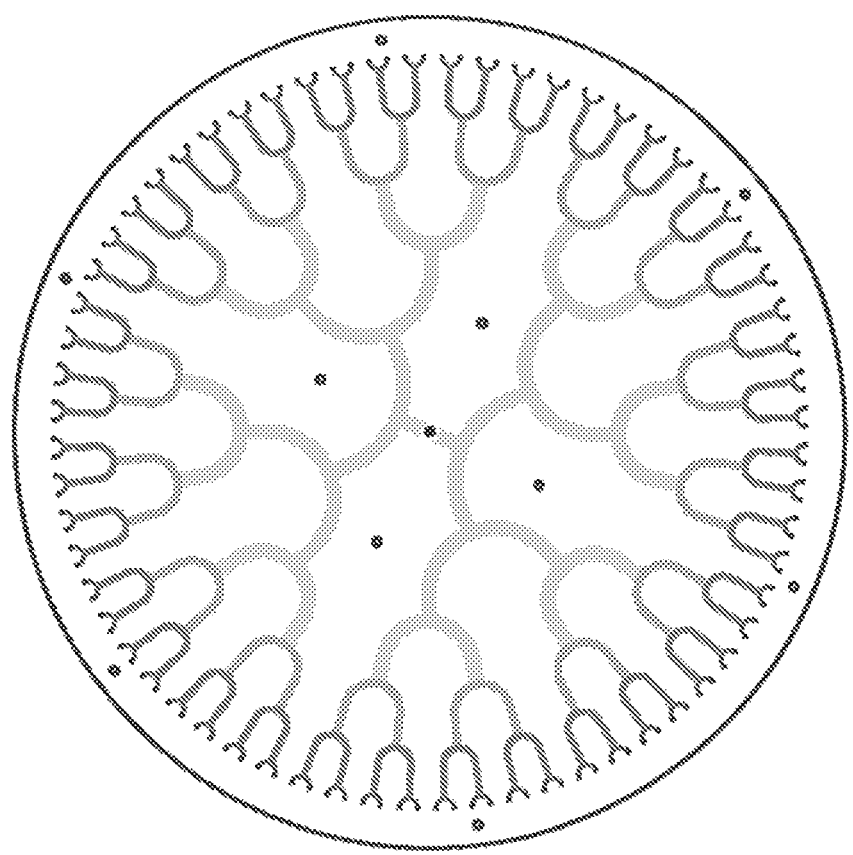
FIG. 6 shows disperse phase distribution network and distribution network.

FIG. 3 shows an assembled stack. FIG. 4 shows a cap layer or a top layer. This layer closes the channels of the Continuous Phase Distribution network. FIG. 5 shows continuous phase distribution network. In this figure, each channel subdivides into two channels progressively; fractalized distribution network has a single inlet in the center. The continuous liquid is fed from the top of the stack and from the center to the edge of the disk. FIG. 6 shows disperse phase distribution network. In this figure, each channel subdivides into two channels progressively; fractalized distribution network has a single inlet in the center. The liquid to be dispersed is fed from the bottom of the stack and from the center to the edge of the disk.

Figure 7:
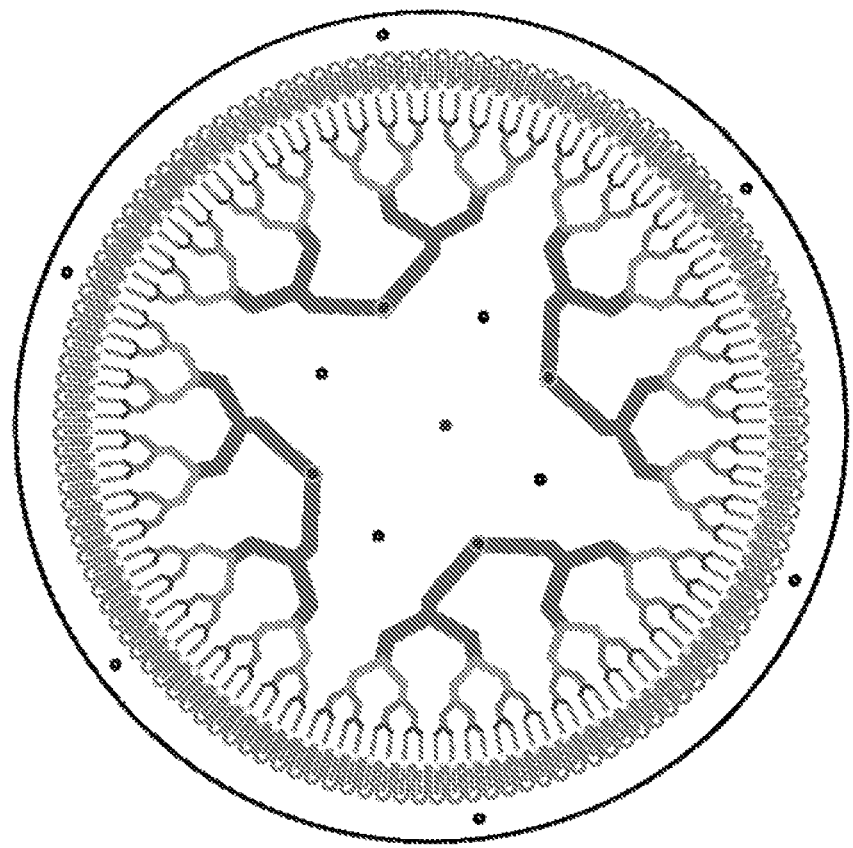
FIG. 7 shows a first layer of generators, or a bottom layer.
Figure 8:
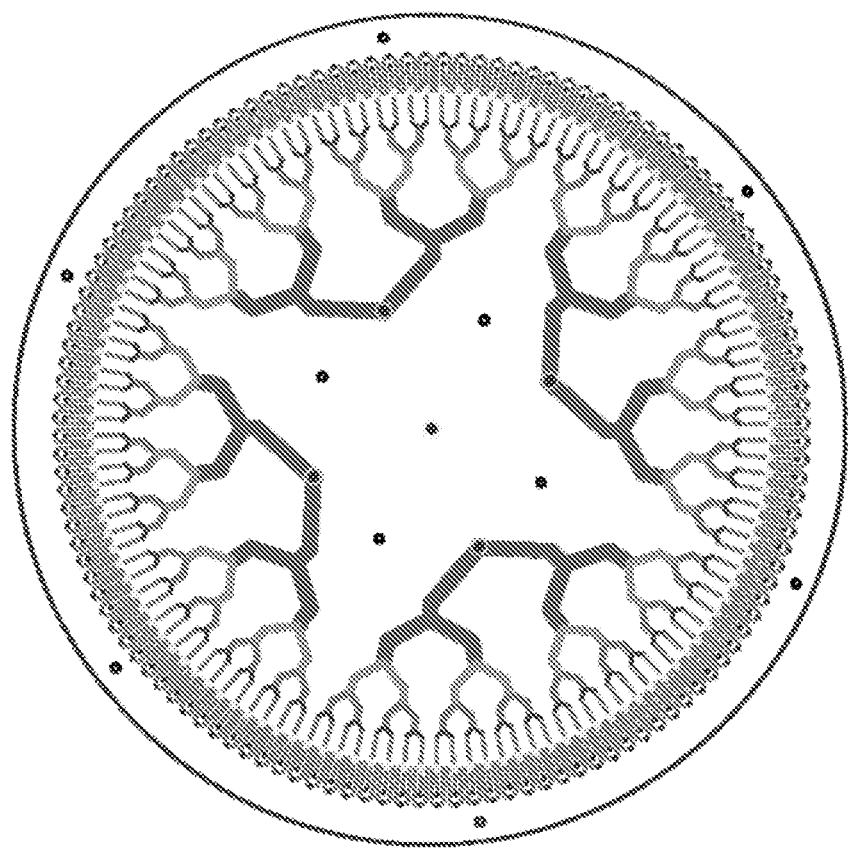
FIG. 8 shows an intermediate layer of generators. For example, it can be a second layer, a third layer, a fourth layer, etc.
Figure 9:
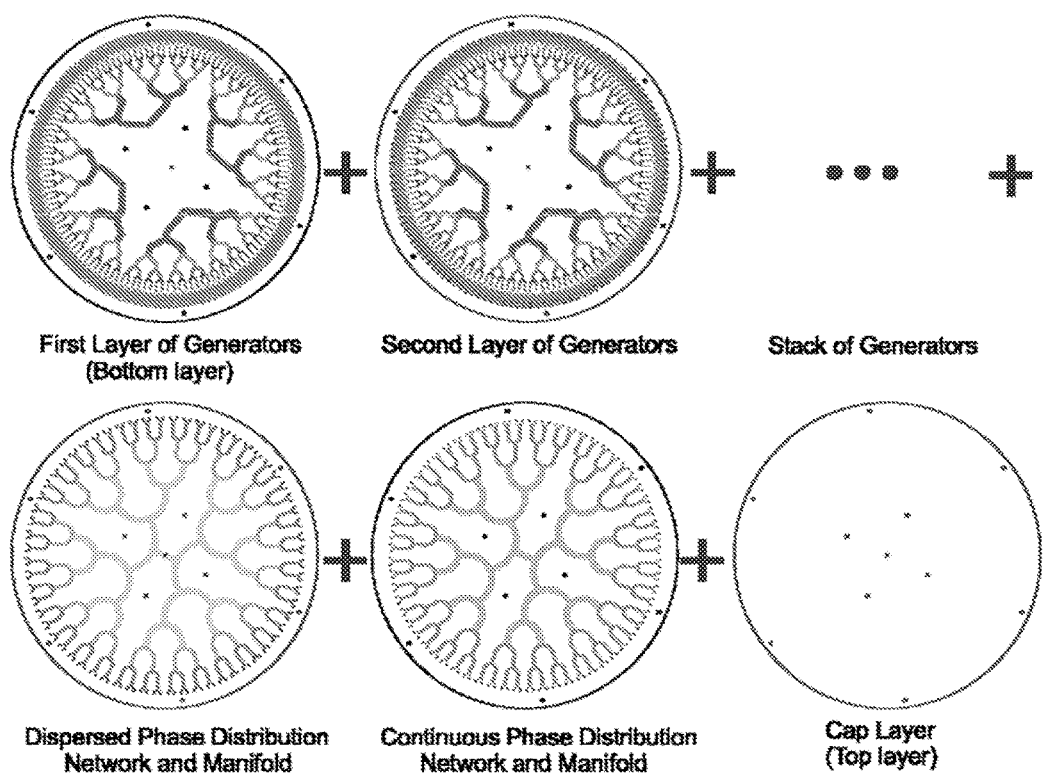
FIG. 9 shows different layers that form the device.
Figure 10:
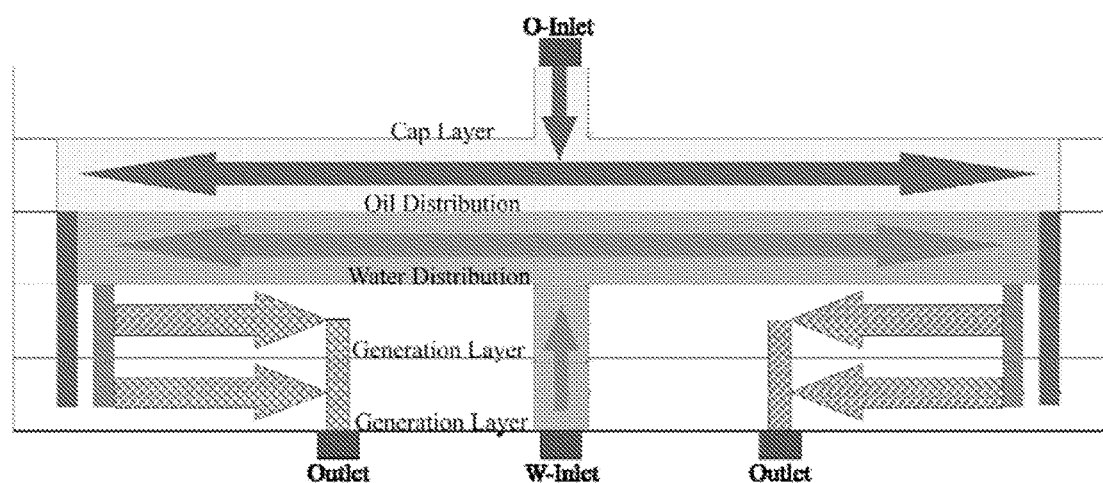
FIG. 10 shows a schematic how the liquid phases flow from the inputs to the generators through the distribution layers.
Figure 11:
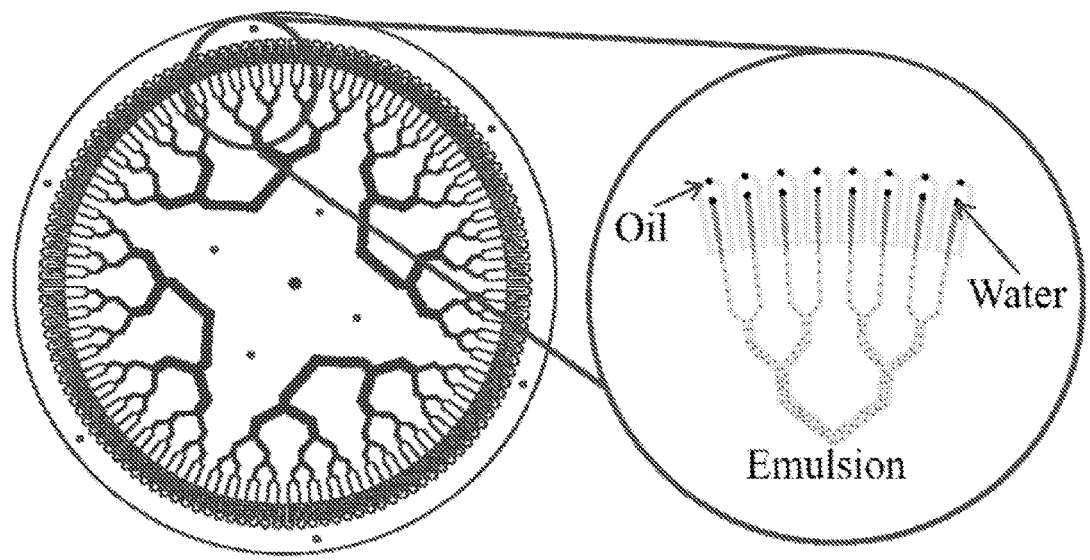
FIG. 11 shows a close up image of how the generators in the generation layers look like when they work simultaneously.

FIG. 7 shows a first layer of generators, or a bottom layer. This bottom layer includes 128 generators. The widths of the channels vary from 250 μm (for the cyan crosses) to 2 mm (the blue-gray). Because of the channel's dimensions, 128 microfluidic droplet generators can be fitted. With narrower channels, any number that can be fractalized can be fitted and fed with a distribution network. For example, the number can be $p \times m \times 2^n$, where p is an integer representing the number of petals, m is an integer representing the number of identical generation layers and n is an integer representing the number of levels of the fractal branching generators arranged in a polar array. FIG. 8 shows a second layer of generator. This layer can be the same as first layer of generators. This layer has two connecting through-holes for each droplet generator (for example: 500 um diameter) to communicate them to other layers, integrating the distribution network. This layer can be fabricated multiple times to scale the number of generators. FIG. 9 shows different layers that form the device and describes how the stack is formed. The bottom layer is the first layer of generators and the top of the stack is the cap layer. The stacked disk can have a diameter of 110 mm. The device can include any two immiscible fluids that lend themselves to droplet formation. One fluid can be the "disperse phase", the fluid that is turned into droplets. For example, water, or an aqueous solution (glycine in water), can be used as a fluid. The other fluid can be the "continuous phase", which is the phase that shears or cuts the droplets, and carries the droplets. For example, dodecane or mineral oil with surfactants can be used as a fluid. In one example, the device can include a water distribution layer. In another example, the device can include an oil-distribution layer. The device can include a cover layer. The thickness of each layer can be less than a few millimeters, for example, less than 1 mm.

A stacking of arrays of generators can be integrated in a single chip. A three dimensional microfluidic device can include a distribution network connecting a stack of emulsion generation layers. The distribution network can include at least two distribution layers, each one including at least a fractal pattern of fluidic channels and through holes interconnecting them with the other stack layers. The number of the generation layers can be any integer number, preferably 1-100, preferably 1-50, preferably 1-25, and preferably 1-10. The generation layers can be formed by a polar array of microfluidic droplet generators. A method for preparing an emulsion comprising using a multi-layer microfluidic device comprising at least two layers, wherein at least one layer includes a rigid polymer, wherein the two layers are connected by through-holes, wherein each layer includes a fractal pattern, and wherein each layer includes a distribution network connecting with channels of the device to control the flow of a fluid. The emulsions can be monodisperse. The production rate of the emulsions can be at least 300 mL/h.

Petal Organization

Figure 18:
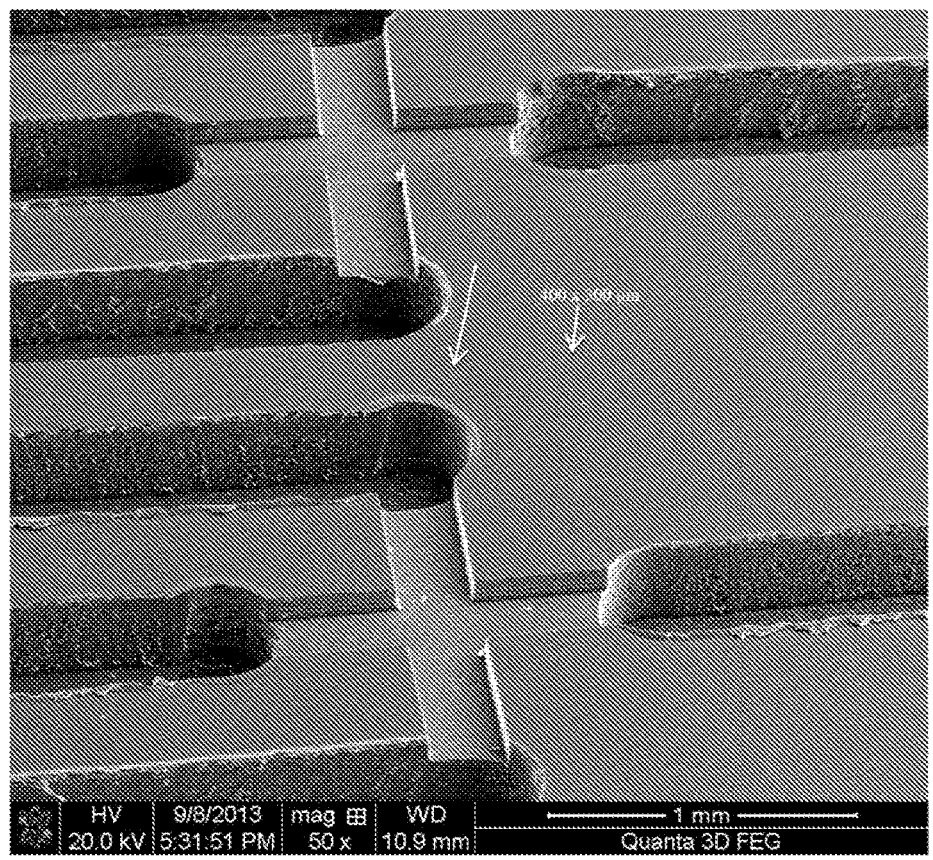
FIG. 18 shows an SEM picture of microfluidic channels cut on PMMA.

The flow-focusing parallelized MFDG can include a ~250 µm-wide by ~100 µm-deep cross-shape constriction that connects with a wider and deeper channel (400 µm-wide by 300 µm-deep) downstream (FIG. 18). The wide and shallow rectangular geometry was previously simulated (see, D. Conchouso, E. Rawashdeh, D. Castro, A. Arevalo and I. G. Foulds, Optimized Channel Geometry of a Flow-Focusing Droplet Generator for Parallelization, Rotterdam, 2013, which is incorporated by reference in its entirety) and proven to be less sensitive to flow changes than other geometries with an equivalent hydraulic diameter thus making it appropriate for parallel systems.

Massive parallelization of MFDGs can include stacking layers of the equation $p \times m \times 2^n$, where p is an integer representing the number of petals, m is an integer representing the number of identical generation layers and n is an integer representing the number of levels of the fractal branching generators arranged in a polar array. A device can include one, two, or four, more generation layers containing 128 MFDGs each. A greater number of MFDGs per layer is possible by using fabrication processes with a higher feature resolution like photolithography or by increasing the total area of the device.

Using a third dimension for parallelization brings important advantages over two-dimensional expansion. Each layer of a multi-layer device can have any thickness depending on the size of channels. The layer can have the minimum thickness required to adopt the desired sized of channels for the effective distribution network and compact system design for high-density packing of MFDGs.

Figure 14:
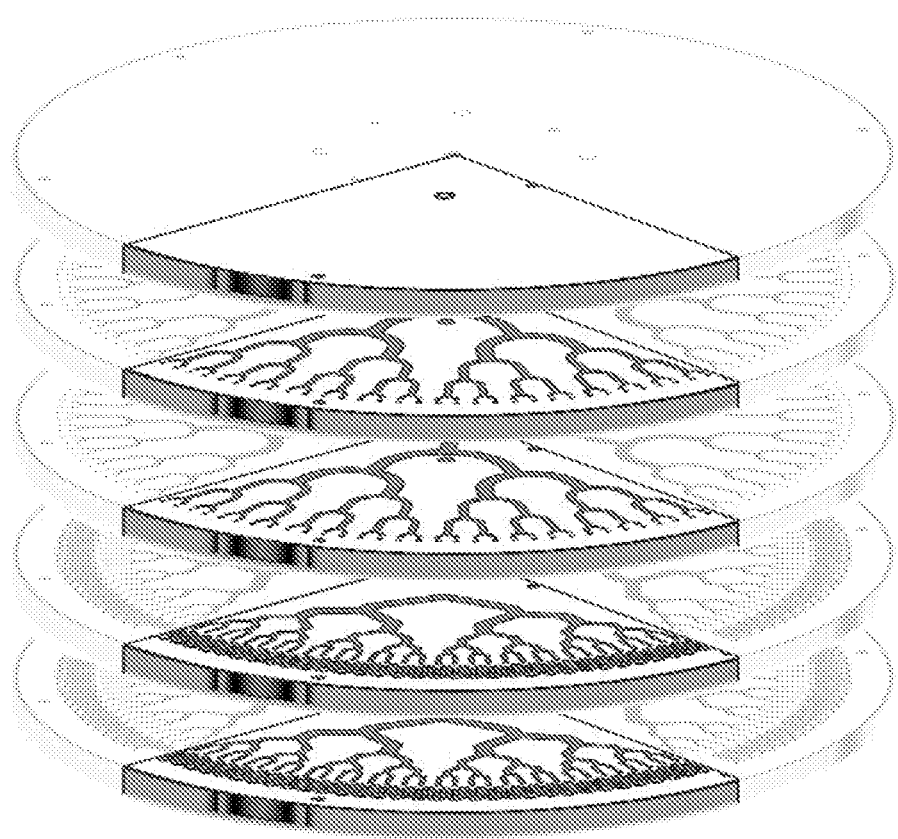
FIG. 14 shows a petal configuration illustrating how petals act as independent units within a chip.

A parallelization chip can be composed of four basic layers: cap layer, oil-distribution network, water-distribution network, and droplet generation layer. Additional droplet generation layers can be incorporated to the stack for further scaling up of MFDGs (FIG. 14). The different layers can be all connected with each other by through-holes that are fabricated along with the device and allow the integration of the distribution network within the chip. Several designs for the distribution layers were tested: tree-like fractal distribution network, annular distribution network, and a combination of both. Only the first one proved to be a reliable structure and provided the best results for this parallelization chip.

For the tree-like fractal distribution network depicted in FIGS. 2 and 14, input ports for both liquids can be axisymmetrically placed in the center of the stack at the top and on the bottom of the chip in order to maintain the same channel length from the liquid source to the MFDGs in all directions in the disk. Alternatively, input ports can be placed at any point and then directed to the middle for the initial distribution. Both liquids flow from the center to edge of the disk and then proceed from the top to lower layers. If additional phase inputs are required, two extra layers per input must be added in order to maintain this centralized distribution (i.e. one for distribution and one from the input to the center of the disk).

Figure 23:
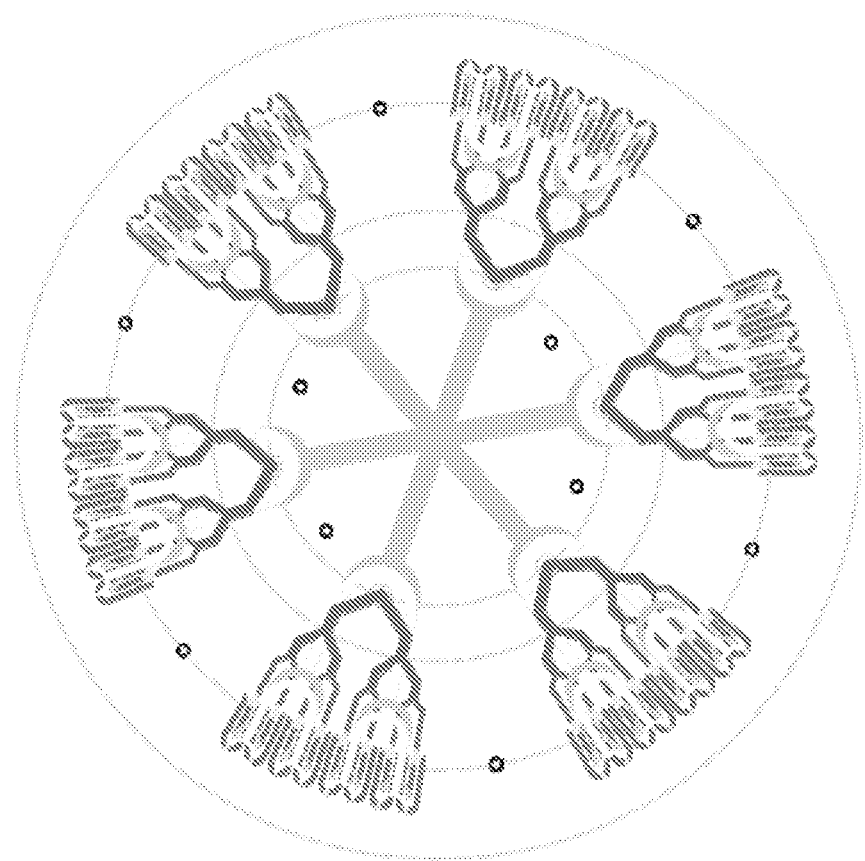
FIG. 23 shows an example of a device with 6 petals where each petal has eight generators.

Coupling of the parallel MFDGs occurs through the distribution networks and at the output of the system. The design can include organizing the polar array of MFDGs in four groups or 'petals' that can be treated as independent blocks of droplet generation within the same chip, each one with its own designated output (FIG. 14). Crucially, these petals are only connected with each other at the highest level of hierarchy (adjacent to the input port), where the coupling and impedance are minimum. Because of this, shutting off one of these sections (petals) has little to no effect on the others, and therefore on output production. A petal is formed $2^n$ MFDGs in the case of the device shown in FIG. 14 (disk stack with a petal highlighted on red), each petal has 32 MFDGs per layer. FIG. 23 shows an example of a device with 6 petals where each petal has 8 generators.

A major concern when working with parallel systems is the latent possibility of clogging, especially when dealing with systems containing tree-like distribution networks since they have been reported to have greater sensitivity to random resistance changes.

In the proposed petal-like structure, groups of MFDGs sharing a common output act as independent units within the same chip. If one section gets clogged and its output becomes suddenly polydisperse, one can close the affected petal by closing either its two input branches or one input branch and the output. The channel resistance of a closed petal becomes infinite and by adjusting the input pressure to retain the original flow per MDFG, the other outputs can still maintain their low dispersity and size. A parallel system with this type of petal structure can then work with a deactivated section and avoid a total production halt.

Figure 15:
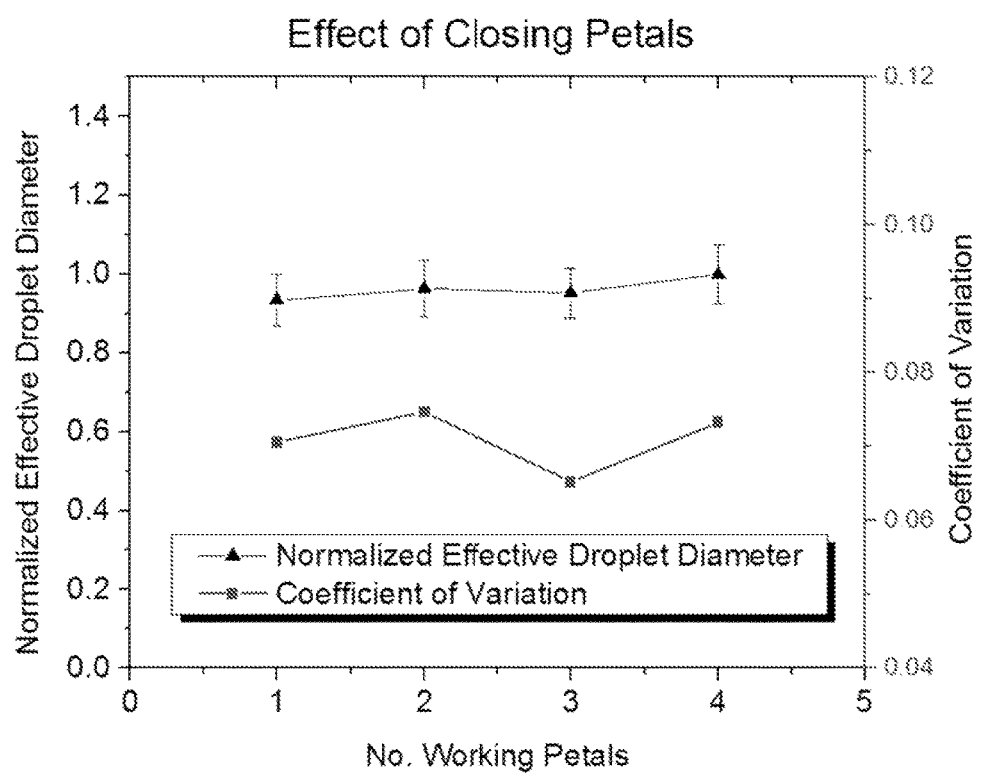
FIG. 15 shows a graph depicting the effect on the dispersity of the emulsion when closing different number of petals

FIG. 15 shows the effect of closing a clogged section, the size distribution of the output generated by the "256-Device I" was measured when one, two or three of its petals were completely closed, as compared to its output with all petals functioning. The result shows that by adjusting to the correct pressure, a similar droplet size and dispersity can be maintained, which demonstrates the advantage of the petal structure. As independent functional units, which have weak mutual influence, petals can be deactivated and reactivated, if proper valves are implemented.

An individual sensor can be also implemented to monitor the petal functioning. Using an individual sensor enables a system where one of some of the sections (or petals) of the device can be closed while keeping the other sections (or petals) working with little to no change. Some of the possible methods for detecting a clogged petal (section) can be monitoring the inputs or outputs of all the petals in the device to see if they all operate without change. Sensors that can help with detecting changes in the finalized product and that can be used as feedback systems to close the petals can include RF structures, capacitance sensors, image processing (optical inspection), impedance measurements, flow sensors, pH sensors, light scattering sensors (e.g. lasers), interfacial sensors, and viscosity sensors.

This behavior is expected to be seen in devices with different numbers of generation layers and is independent of the number of petals per layer. It is worth noting that these petals are only connected with each other at the highest level of hierarchy (adjacent to the input port), where the coupling and impedance are minimum. Because of this, closing one of these petals has little to no effect on other petals and therefore on production output.

Post-Droplet Generation Processing

Batch processing of emulsions, by means of shear forces of two immiscible phases, has been used in the industry for a long time. However, a microfluidic system offers advantages over its batch production counterpart. For example, the microfluidics approach can control the exact amount of reagents, the mixing rate, the residence time, the environmental conditions and the post-processing of these emulsions at the granularity of a single droplet. Some of these approaches have been discussed. See, for example, G. T. Vladisavljevic et al., Industrial lab-on-a-chip: Design, applications and scale-up for drug discovery and delivery, *Advanced Drug Delivery Reviews*, July 2013; C. Holtze, *J. Phys. D: Appl. Phys.*, vol. 46, no. 11, p. 114008, February 2013; C. X. Zhao, Multiphase flow microfluidics for the production of single or multiple emulsions for drug delivery, *Advanced Drug Delivery Reviews*, 2013; Tetradis-Mairis et al. Method and apparatus for producing microparticles WO 2010025988 A1; Nisisako et al. Apparatus for producing micro liquid drops, EP 2594332 A1; Kumacheva et al. Multiple continuous microfluidic reactors for the scaled up synthesis of gel or polymer particles, WO 2008148200 A1; Mark B Romanowsky et al. Scale-up of microfluidic devices, WO 2010104597 A2, each of which is incorporated by reference in its entirety.

A microfluidic system can include a post-droplet generation processing step implemented through a closed curved surface, such as a tube, a funnel or a cylinder, for high-volume continuous productions of any kind of particles. The post-processing step can be any process that can modify the structure and composition of the droplets. For example, this step can include a heating mechanism to accelerate synthesis of materials, a UV exposure zone for polymerizing UV sensitive particles, or other materials, plasma treatment, passing through a different gas atmosphere, for example, a reactive gas, electric discharge, freezing, or any other treatment that can transform the droplets into particles.

Figure 16:
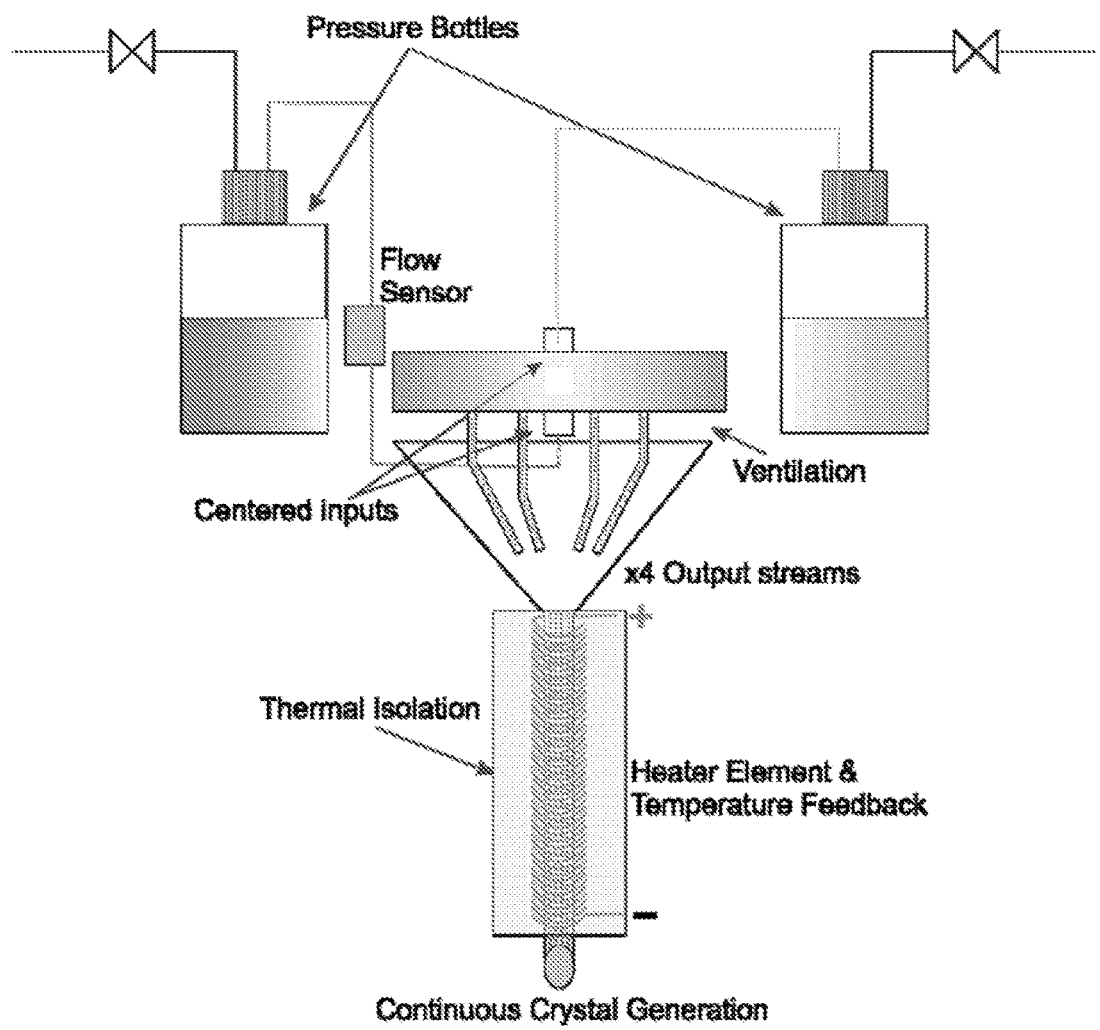
FIG. 16 and FIG. 17 show examples of an experimental setup for the massive parallelization of microfluidic droplet generators, where the setup includes a post processing stage in which the output emulsion can be treated.
Figure 17:
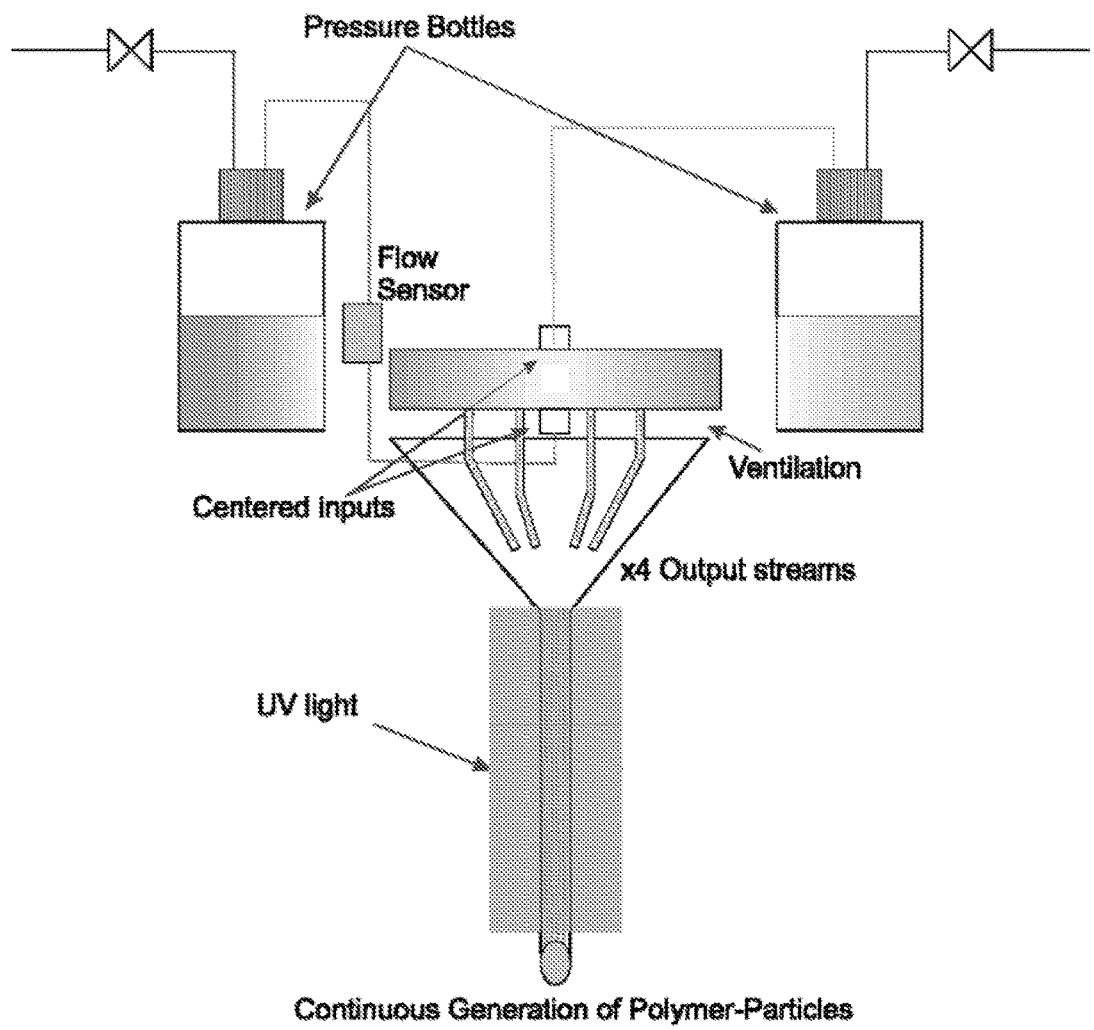
Figure 21:
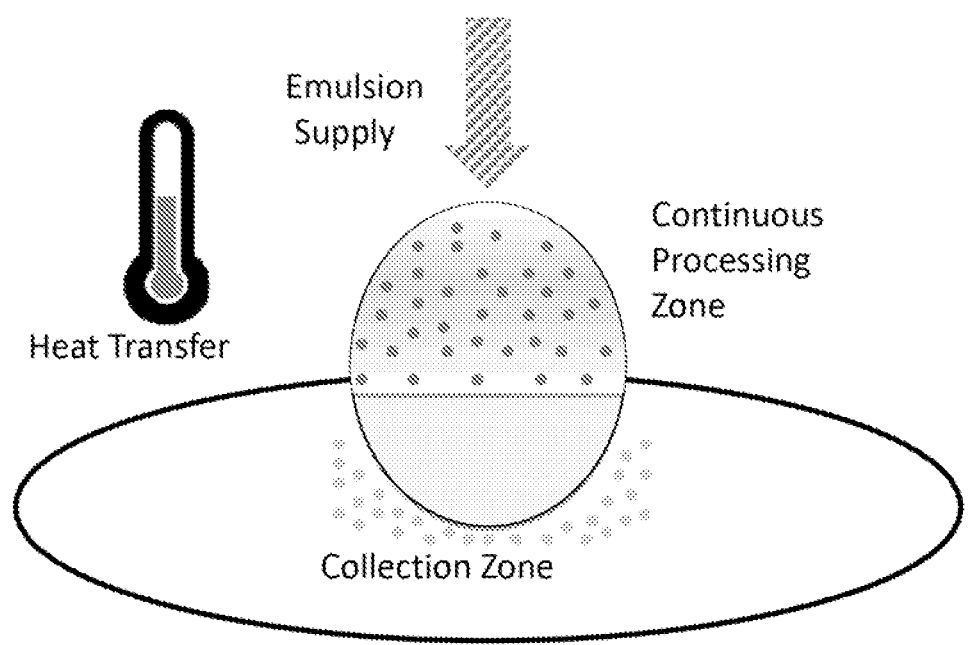
FIG. 21 shows a schematic of post-processing in an opened round surface.
Figure 22:
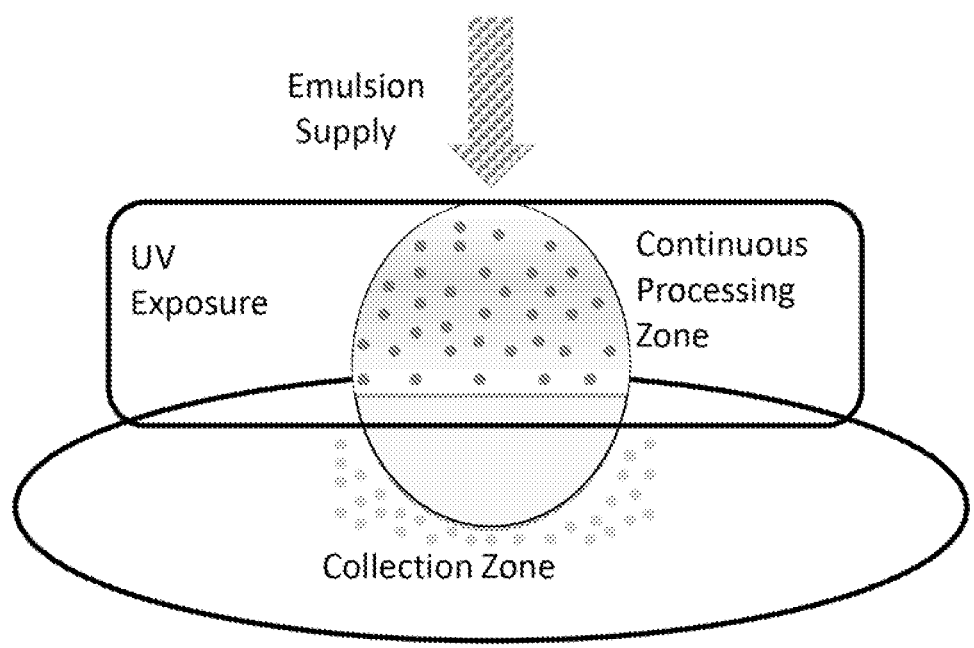
FIG. 22 shows a schematic of UV post-processing in an opened round surface.

The post-processing step can include forming a continuous flow of emulsion that can slide down on the glass walls of a closed curved surface of a tube or a funnel (FIGS. 16, 17, 21, and 22). FIG. 16 shows an experimental setup for the massive parallelization of microfluidic droplet generators. The four outputs of the generator can be aligned around a glass funnel or tube and their throughput slides on the wall of the tube or funnel and wets the entire perimeter of a cross section the column. The funnel or tube can be used as an extended diameter for post-processing steps, such as a heating step. FIG. 21 shows an experimental setup for post-processing in an opened round surface. FIG. 17 shows an experimental setup for the massive parallelization of microfluidic droplet generators. The four outputs of the generator can be aligned around a glass funnel or tube and their throughput slides on the walls of the tube or the funnel and wets the entire perimeter of the column. The funnel or the tube can be used as an extended diameter for post-processing steps, such as a UV exposure. FIG. 22 shows an experimental setup for UV post-processing in an opened round surface.

A method for preparing an emulsion can include supplying a fluid from a mixer to a particle fixation zone, or a processing zone, having a curved surface such that the fluid forms a layer free of side edges. A method for supplying a fluid can include heating a layer of the fluid without an edge. The zone can include a tube having a curved surface, where liquid supplied from outputs passes through the tube, contacts the wall of the curved surface, and can wet the entire perimeter of the curved surface. A particle fixation zone, or a processing zone, can be exposed to an ultraviolet light or heated. A method for preparing an emulsion can include supplying a fluid from a mixer to a processing zone having a curved surface such that the fluid forms a layer free of side edges.

A system for processing an emulsion can include a tube and at least one output supplying the emulsion through the tube. The system can include at least one output supplying fluid; the system can include at least four outputs supplying fluid. Outputs can include a plurality of outputs aligned around the closed curved surface. The fluid can wet the entire perimeter of the tube. The system can be connected to a multi-layer microfluidic device. The system can heat a layer of the fluid without an edge. The post-processing step can be a major step toward scaling microfluidic production of drug crystallites to an industrially relevant scale.

Advantages of the Device and System

There are advantages for a multi-layer microfluidic device that includes at least two layers, wherein at least one layer includes a rigid material, wherein the two layers are connected by through-holes, wherein each layer includes a fractal pattern, and wherein each layer includes a distribution network connecting with a channel of the device to control the flow of a fluid. The rigid material can include polymer, glass, or silicon. The advantages of this device includes that it can be made in a rigid material (PMMA). This contributes to the proper alignment of the MDGs in the fabrication process and facilitates the stacking of devices. It also reduces the hydraulic capacitance due to the low deformation of the devices when a pressure change is applied, by doing so it can show a better and faster transient response. A glass and/or silicon or any polymer substrate can also be used.

Another important advantage of PMMA, COC, COP, PT, PC, glass and/or silicon over PDMS is their lower adsorption and absorption to chemicals and their low gas permeability.

In addition, the axisymmetric inputs for liquid phases can be centered and can be accessed from the top and the bottom surfaces of the disk, providing an even and direct distribution of the fluids to the individual stacks of droplet generators. This makes a clean and fast loading of the liquids and avoids the trapping of undesired bubbles. The system can fully integrate the distribution network within the microfluidic chip, so it only requires the two inlets for the different phases discussed above. This offers a greater flexibility in design and 3D integration for massive stacking than any other of the designs presented before.

This device and system can provide the largest throughput for a single device reported in the literature (Flow rate of the disperse phase $FR_{dp} \cong 300$ ml/h) for a 256 channels device. The throughput can be further improved by adding more microfluidic droplet generator arrays in additional stacking layers.

The increased number of outputs (4 or more) allows control the streams of monodisperse emulsions and guides them to form a thin emulsion layer that slides over a large-diameter funnel or tube in order to handle a higher production and post-processing steps. Post-processing steps include heating, exposure to an ultraviolet light, etc.

Example

Fabrication Process

The multi-layer parallelization chip is made out of a 1 mm-thick sheet of cast PMMA, an inexpensive material commonly used in microfluidics. The Computer Numerical Control (CNC) micromilling and the thermo-compression bonding presented herein make up a fabrication process for rapid prototyping of three-dimensional microfluidics. The direct micromilling process of the microfluidic channels can be easily implemented in any high-precision CNC machine and does not require a clean room facility. Moreover, inexpensive PMMA bonding has been demonstrated using several successful methods ranging from thermo-compression bonding, microwave bonding, low temperature ultrasonic bonding, and through surface modifications. See, X. Zhu, G. Liu, Y. Guo and Y. Tian, *Microsyst. Technol.*, 2006, 13, 403-407, Y. Sun, Y. C. Kwok and N.-T. Nguyen, *J. Micromech. Microeng.*, 2006, 16, 1681-1688, M. Rahbar, S. Chhina, D. Sameoto and M. Parameswaran, *J. Micromech. Microeng.*, 2009, 20, 015026, R. J. Holmes, C. McDonagh, J. McLaughlin, S. Mohr, N. J. Goddard and P. R. Fielden, *J. Phys. Chem. Solids*, 2011, 72, 626-629, S. W. Li, J. H. Xu, Y. J. Wang, Y. C. Lu and G. S. Luo, *J. Micromech. Microeng.*, 2009, 19, 015035, and L. Brown, T. Koerner, J. H. Horton and R. D. Oleschuk, *Lab Chip*, 2006, 6, 66, each of which is incorporated by reference in its entirety.

An MFDG can include a 100 μm-deep cross-shape constriction that connects with a wider and deeper channel downstream. FIG. 18 shows an SEM picture of microfluidic channels cut on PMMA using a standard PCB milling machine for producing rapid prototypes. The cross-shape constriction is 1000 μm-long×260 μm-wide×100 μm-deep. Feed-lines and outputs are 400 μm-wide×300 μm-deep.

A chip can be directly machined on a 1 mm-thick sheet of cast-PMMA using an LPKF ProtoMat-S103 PCB plotter. The LPKF system has an x-y resolution of ±0.5 μm and is equipped with a depth delimiter that reduces the depth variation across the chip below ±10 μm, depending on the substrate flatness. All of the interconnections between the stacking layers are also CNC drilled as part of the same process. The surface roughness of the channels was measured with an Ambios XP-200 step profiler and the surface roughness was ~140 nm at the cross-shaped constrictions and ~350 nm at the distribution channels, which are negligible as compared to the measured fabrication error of the device (Table 3).

TABLE 3

Devices tested with their respective fabrication variability

| Device | Constriction depth | Fabrication st. dev. (σfab) |
|---|---|---|
| 128-Device I | 94 μm | 4.8% |
| 128-Device II | 78 μm | 7.9% |
| 256-Device I | 102 μm | 4.21% |
| 512-Device I | 105.6 μm | 4.38% |

Once the generator and distribution layers are milled, the stack of layers can then be brushed with soapy water, rinsed and pin-aligned for bonding. Visual inspection is necessary to guarantee that no residue left from the milling process is blocking any of the channels. The stack of layers is then assembled using alignment pins (for accurate alignment ≤5 μm) and thermo-compression bonded using an Instron 5900-Series fitted with an environmental chamber. The stack of layers can then be thermally bonded at 150° C. under compressive stress (12N/cm$^2$) for 45 min using an Instron 5900-Series provided with an environmental chamber. The temperature is then dropped gradually below 50° C. while the compression stress is maintained constant for another 15 min. Finally, world to chip interfaces and tubing are glued on the parallelization disk. Chip-to-world connections can be included in the top and bottom layers.

Although there is no noticeable deformation in the microchannels after bonding, it should be noted that the cap layer can be extruded into the channel by 5 to 10 μm. Very shallow and wide channels may therefore be blocked by this bonding process. The bonding strength, however, was tested to withstand high pressures (~7.5 bar), well above the pressures normally used in the loading sequence of the device to eliminate trapped bubbles. This process is low cost and offers the capability to parallelize in the third-dimension with accurate alignment.

Materials

For imaging and droplet characterization, decane (≥99%) was used as a continuous phase (CP), with a 2% (w/w) surfactant mixture consisting of 70% Span-20 and 30% Span-80 (w/w). The dispersed phase (DP) was a solution of Ultrapure Millipore Milli-Q DI water (18.3 MΩ) with red food coloring that was added to enhance the contrast and to facilitate the characterization of the single emulsion through an image processing software. See, A. S. Basu, *Lab Chip*, 2013, 13, 1892-1901, which is incorporated by reference in its entirety. Particle crystallization was also achieved using dodecane (≥99%) as a CP with the same surfactant content described above and glycine (>99%) solution saturated at room temperature (22° C.) as a DP. This solution has approximately 24.4 g of glycine content per 100 g of DI water. See, K. Allen, R. J. Davey, E. Ferrari, C. Towler, G. J. Tiddy, M. O. Jones and R. G. Pritchard, *Cryst. Growth Des.*, 2002, 2, 523-527, which is incorporated by reference in its entirety. All solutions were filtered before each experiment using Cole-Parmer syringe filters (0.45 μm).

Experimental Setup

Figure 13:
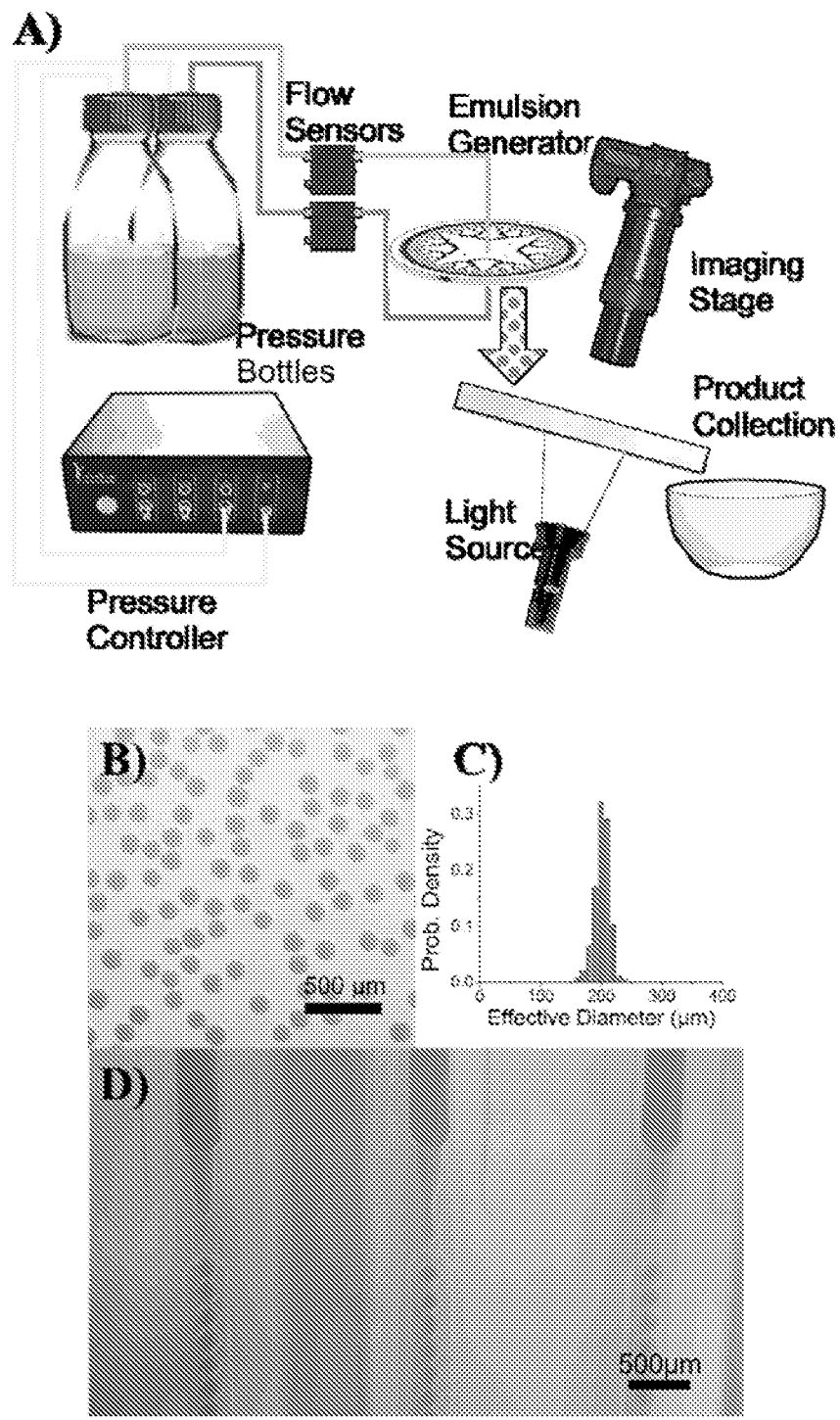
FIG. 13A shows an example of an experimental setup for the massive parallelization of microfluidic droplet generators, where the setup includes a post processing stage in which the output emulsion can be treated.
FIGS. 13B and 13D show images of an example of dyed water-in-oil emulsion for easy visualization.
FIG. 13C is a graph depicting the effective diameter distribution.

A schematic of the experimental setup is presented in FIG. 13. Both the CP and DP were loaded into separate containers and then connected to an Elveflow OB1 pressure pump to control the pressure in the fluid reservoirs in the range of 0-2000 mbar. Flow sensors, connected to the OB1, were used to monitor the flow rates. In order to run the experiment, the parallelization chip was placed on top of a glass funnel that helps direct the output flow to a white plastic surface for imaging. This surface works as a good light diffuser to facilitate uniform lighting conditions.

Figure 19:
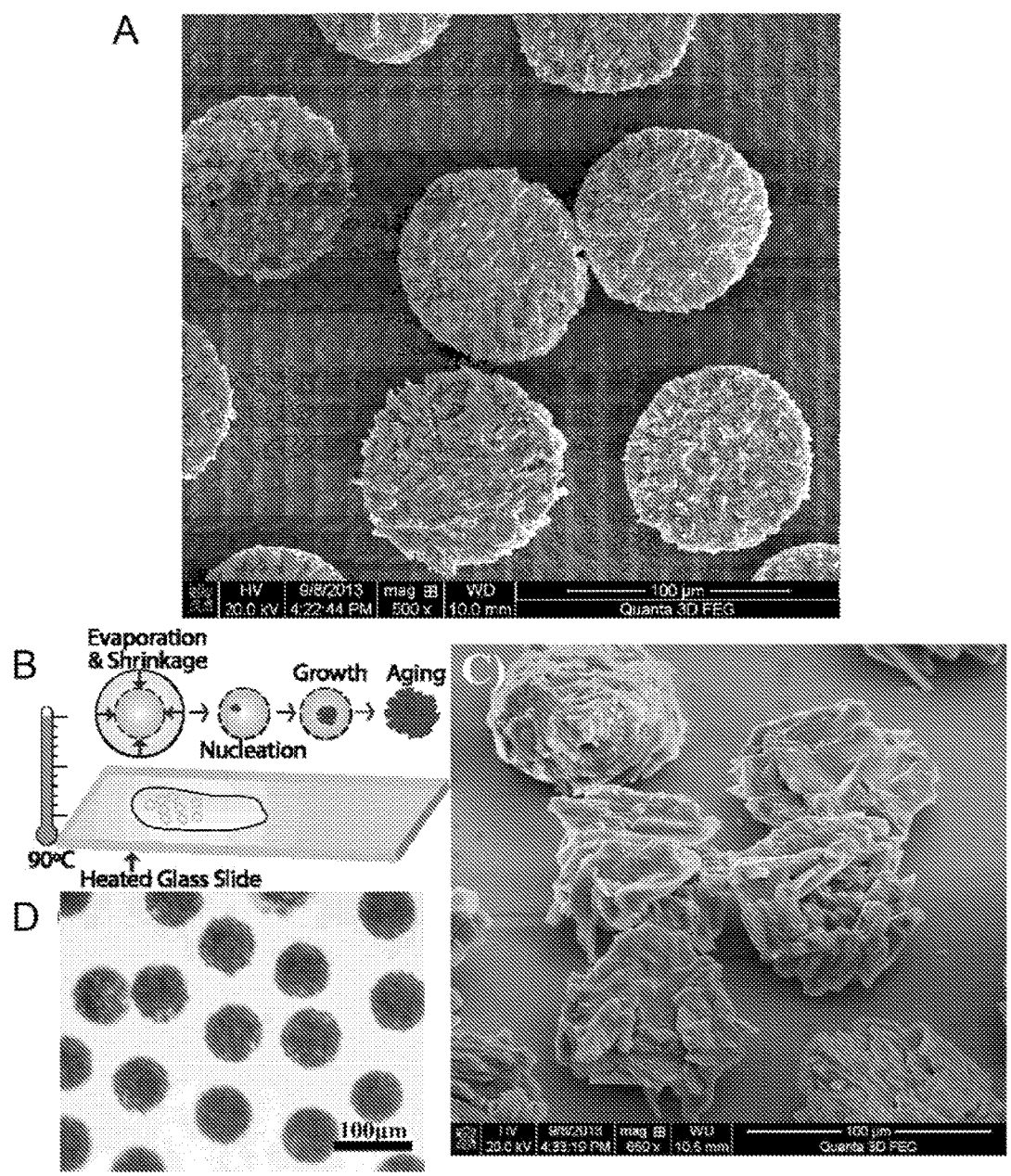
FIG. 19 shows a crystallization of glycine spherical crystal agglomerates.

An Elveflow OB1 pressure-pump with flow sensors was used to control the pressure in the fluid reservoirs within 0.03-0.7 bar to fill and then bring the system to steady state production. To achieve high throughput water-in-oil emulsions the continuous phase was a solution of dodecane >99% with 2% surfactant comprised of 70% Span 20 and 30% Span 80 and the water phase solutions were one of dyed water as well as one of glycine-loaded water. The dyed water-in-oil emulsion was imaged, as shown in FIG. 19, to examine the dispersity of the emulsion. The dispersity of the emulsion was examined using the DMV software. See, for example, A. S. Basu, "Droplet Morphometry and Velocimetry (DMV): A video processing software for time-resolved, label-free tracking of droplet parameters," *Lab on a Chip*, 2013, which is incorporated by reference in its entirety.

FIG. 19 shows an example of dyed water-in-oil emulsion for easy visualization. A Canon 5D camera with MPG65 mm macro lens was used to image the output. During the tests, on average 100 high quality pictures (21 Mpx) were taken for each data point. These pictures were then transformed into AVI video files and processed on a droplet morphometry and velocimetry software (DMV). Typically, the effective droplet diameter distribution for the experiments was obtained from a sample of ~8000 droplets, which represents a statistically significant sample for very large populations.

Loading Sequence and Distribution Network Configurations

Figure 20:
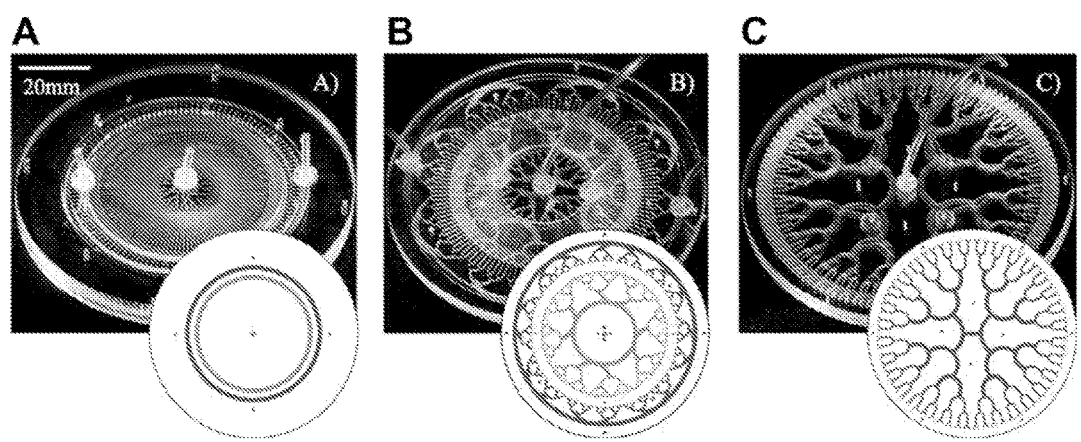
FIG. 20 shows examples of distribution networks.

Uniform liquid loading plays one of the most critical roles in the parallelization of MFDGs. Loading problems may include: pressure gradients across the chip in asymmetric distribution networks, bubbles trapped that modify the flows, back flow of one of the phases into the other, changes in the channel resistances depending on the flowing liquid, clogged channels, and many others. See, G. T. Vladisavljević, N. Khalid, M. A. Neves, T. Kuroiwa, M. Nakajima, K. Uemura, S. Ichikawa and I. Kobayashi, *Adv. Drug Delivery Rev.*, 2013, 65, 1626-1663, and C. Holtze, *J. Phys. D: Appl. Phys.*, 2013, 46, 114008, each of which is incorporated by reference in its entirety. To minimize these problems, three different configurations were tested for this high-throughput microfluidic chip: a coaxial annular network, an annular network combined with a tree-like network, and a fractal treelike distribution network (FIG. 20). All network configurations were tested using similar loading conditions. First, both oil and aqueous phases are pushed in at high pressure (e.g. ~1000 mbar) to clear all of the trapped bubbles and to ensure a complete loading to all microfluidic channels. Then a decreasing ramp is applied (−65 mbar/s) and the pressure is steadily reduced to 50 mbar. Finally proper tuning is done with the help of the camera and flow sensors by small pressure changes (1 mbar). Optical inspection of droplet formation is possible, thanks to the PMMA's transparency, and allows us to detect possible problems in the system. If an irregularity is noticed, cleaning cycles of high pressure (1-2 bar) are applied in short bursts to clear the obstructions. An advantage of using PMMA as compared to PDMS and other elastic materials is its greater stiffness (Young's modulus 2.4 to 3.3 GPa) that contributes to microfluidic channels with good dynamic response and low hydraulic capacitance. The Elveflow OB1 pressure pump can be programmed to run the entire sequence automatically, including the cleaning cycles that are usually needed 1-3 times.

A problem that appeared consistently in all tested configurations was the random trapping of air bubbles in the MFDGs. In the case of the annular configurations, this problem remained even after several high-pressure cleaning cycles, leading to irregular feeding and polydisperse droplet generation. On the contrary, the fractal tree-like network worked the best to clean the channels by abrupt pressure changes and showed an even loading of the fluids thanks to the axisymmetric inputs. This distribution network showed the best results to arrange the MFDGs into petals which enable shutting down a section of the chip without affecting the output, and also its loading response contributed to the stability of the chip and improved the dispersity of the output.

Droplet Generation at Different Flow Conditions

The first set of experiments was performed to characterize the size and size distribution of the droplets generated. For this section, DI water with food coloring was used as the DP. Images of the generated emulsion were captured and then processed for devices containing different numbers of generation layers.

Figure 12:
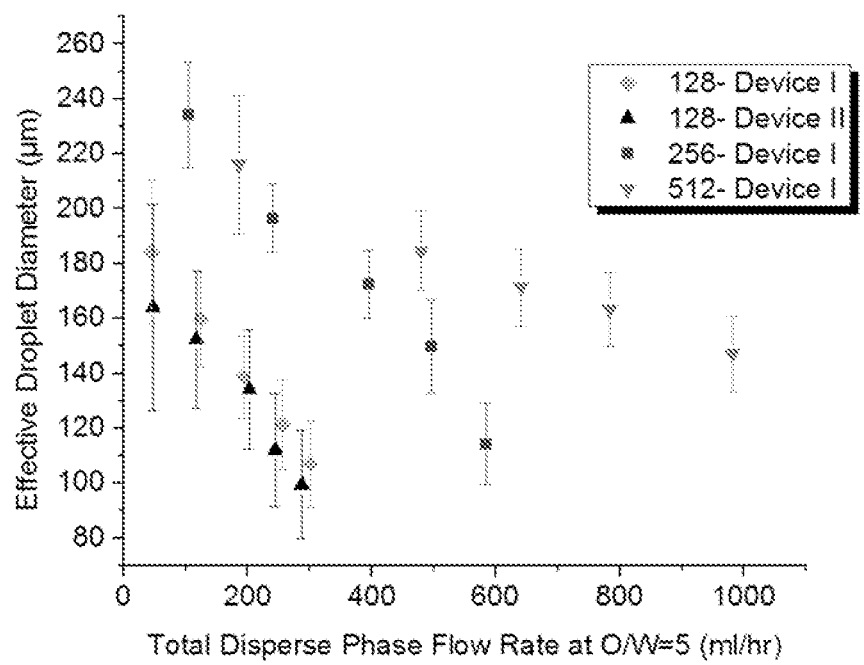
FIG. 12 shows the results regarding size and coefficient of variation of the different multi-layer microfluidic devices tested.
Figure 12:
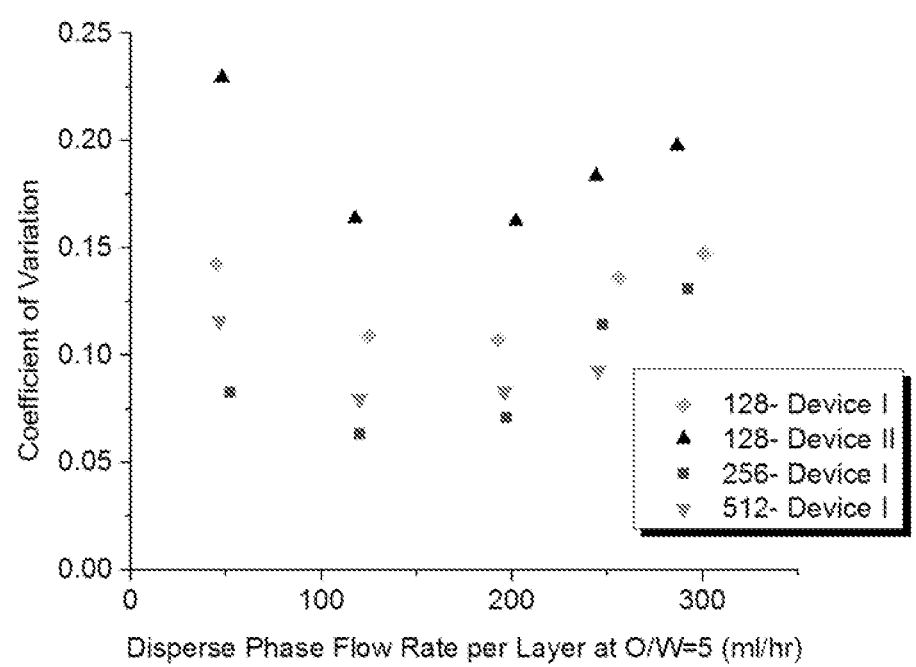

Devices with one (128 MFDGs), two (256 MFDGs) and four (512 MFDGs) generation layers were tested at different total flows while keeping the W/O flow rate ratio constant 1:5 (FIG. 12). Experiments done with devices with 128 and 256 MFDGs operating at a fixed total flow rate and different W/O ratios (1:2, 1:5, 1:10) did not show any significant effect on the size distribution of the emulsion.

For a single layer, the maximum throughput was ~300 ml/h, for a double layer, ~600 ml/h, and for a quadruple layer an output of ~1.2 L/h should be expected. The flow sensors were able to accurately measure up to ~1 L/h. Error bars show the standard deviation of the emulsion for an average sample size of ~8000 droplets (FIG. 12A). The coefficient of variation (FIG. 12B) shows a similar U-shaped curve in all of the devices tested. The double layer device "256-Device I" showed the smallest coefficient of variation among the different devices (Cv=0.06). This device also had the smallest standard deviation in fabrication, which indicates a close relation between the fabrication variability and size distribution variability.

At higher numbers of generation layers, the total flow that passes through the device increases, and therefore the pressure drop across the distribution network increases as well. Because of this, a higher pressure is needed to drive the device. This, however, does not seem to have an effect on the droplet production. As changes in dispersity seem to be dominated by fabrication variability, no direct correlation was found between the coefficient of variation and the number of generation layers.

The maximum operating pressures for devices with 1, 2 and 4 layers are 83, 203, and 500 mbar, respectively. This increase in the driving pressure does not raise concerns for delamination even for high layer count devices. For example a 10-layer device would require ~1.8 bar by extrapolating from the pressure measurements. This estimation is still well below the maximum tested pressure of 7.5 bar that the devices can withstand without delamination.

Two devices with 128 MFDGs each were used to study how the fabrication variability affects the dispersity of the product (Table 3). "128-Device I" had a low fabrication standard deviation of 4.8% compared to "128-Device II" ($\sigma_{fab}$=7.9%). Both devices showed similar characterization curves; however the coefficient of variation produced by the second device increased at each point and was consistent with the fabrication variation change (FIG. 12B).

A change in the dispersity of the output due to fabrication tolerances is to be expected. This issue has been discussed for the case of scaling of parallel devices, since the hydraulic resistance in a channel with a square cross section scales to the fourth power with the channel dimensions. See, G. Tetradis-Meris, D. Rossetti, C. Pulido de Torres, R. Cao, G. Lian and R. Janes, *Ind. Eng. Chem. Res.*, 2009, 48, 8881-8889, and H. Bruus, *Theoretical Microfluidics*, Oxford University Press, 2007, vol. 18, each of which is incorporated by reference in its entirety.

Decoupling of MFDGs Through Petals

A major concern when working with parallel systems is the latent possibility of clogging, especially when dealing with systems containing tree-like distribution networks since they have been reported to have greater sensitivity to random resistance changes. See, G. Tetradis-Meris, D. Rossetti, C. Pulido de Tones, R. Cao, G. Lian and R. Janes, *Ind. Eng. Chem. Res.*, 2009, 48, 8881-8889, which is incorporated by reference in its entirety.

In the proposed petal-like structure, groups of MFDGs sharing a common output act as four independent units within the same chip. If one section gets clogged and its output becomes suddenly polydisperse, one can close the affected petal by closing either its two input branches or one input branch and the output. The channel resistance of a closed petal becomes infinite and by adjusting the input pressure to retain the original flow per MDFG, the other outputs can still maintain their low dispersity and size. A parallel system with this type of petal structure can then work with a deactivated section and avoid a total production halt.

In order to study the effect of closing a clogged section, the size distribution of the output generated by the "256-Device I" was measured when one, two or three of its petals were completely closed, as compared to its output with all petals functioning. FIG. 15 shows this comparison and Table 4 summarizes the experiments as well as the adjustments in pressure that are needed to keep the similar flow rates per working MFDG after closing the outputs. The error in droplet size is due to the small variation in the flow rates as a result of the pressure adjustments and the stopping and re-loading steps required throughout the experiment.

TABLE 4

Summary of experiments for "256 Device I" at different working capacities

| (%) | Po | Pw | $FR_o$ (mL/h) | $FR_w$ (m/h) | $FR_o/FR_w$ | Droplet size (μm) |
|---|---|---|---|---|---|---|
| 100 | 73 | 14 | 1556 | 338 | 4.6 | 199.97 |
| 75 | 60 | 13 | 1131 | 230 | 4.9 | 190.58 |
| 50 | 50 | 13 | 795 | 172 | 4.6 | 192.62 |
| 25 | 37 | 12 | 403 | 84 | 4.8 | 186.99 |

This study demonstrates that petals are independent functional units, which have weak mutual influence and they can be deactivated and reactivated, if proper valves are implemented.

This behavior is expected to be seen in devices with different numbers of generation layers and is independent of the number of petals per layer. It is worth noting that these petals are only connected with each other at the highest level of hierarchy (adjacent to the input port), where the coupling and impedance are minimum. Because of this, closing one of these petals has little to no effect on other petals and therefore on production output.

Production of Spherical Pharmaceutical Crystal Agglomerates

A microfluidic device can be used to produce drug crystallites. Glycine-loaded emulsions were evaporated on a heated glass coverslip to produce spherical crystal agglomerates (FIG. 19), which are a model for active drug crystallites. The crystallization and formulation of active pharmaceutical ingredients ('API's) in the form of spherical agglomerates are crucial steps towards continuous and sustainable pharmaceutical manufacturing and have been of much scientific and industrial interest in recent years. See, for example, A. I. Toldy et al., Spherical Crystallization of Glycine from Monodisperse Microfluidic Emulsions, *Cryst. Growth Des.*, 2012, 12 (8), 3977-3982, R. A. Leon, W. Y. Wan, A. Z. M. Badruddoza, T. A. Hatton and S. A. Khan, *Cryst. Growth Des.*, 2013, 14, 140-146, and A. Z. Md Badruddoza, A. I. Toldy, T. A. Hatton and S. A. Khan, *Cryst. Growth Des.*, 2013, 13, 2455-2461, each of which is incorporated by reference in its entirety. The coupling of microfluidic emulsion generation to rapid, thin film-based evaporative crystallization is a promising route for the precise fabrication of engineered pharmaceutical formulations. The disclosed system greatly facilitates the translation of such methods to industrially relevant scales of production by providing controlled microfluidic emulsification at liter per hour throughput—a crucial requirement in eventual scale-up processes. FIG. 19A shows an SEM picture of glycine spherical crystal agglomerates that are used as reference model in the pharmaceutical industry. The droplets shrink during the crystallization process.

The formation of glycine crystal agglomerates can be demonstrated by using this system. Glycine (>99%) is an example of an amino acid that can be crystallized from an emulsion and is commonly used as a model molecule in pharmaceutical crystallization. A glycine-loaded emulsion with an effective diameter of 150 μm was generated using the "128-Device I". Then a sample of ~100 μL was guided from the output of the emulsion generator onto a heated microscope glass slide (Corning 75×50 mm) to form a thin film of glycine with an estimated thickness of ~0.2 to 0.4 mm. The microscope slide was placed on top of a Torrey Pines Scientific EchoTherm™ HS65 hot plate and set to a temperature of 90° C. in order to produce glycine crystal agglomerates (FIG. 19).

The crystallization sequence details are provided in A. I. Toldy, A. Z. M. Badruddoza, L. Zheng, T. A. Hatton, R. Gunawan, R. Rajagopalan and S. A. Khan, *Cryst. Growth Des.*, 2012, 12, 3977-3982., which is incorporated by reference in its entirety. Briefly it consists of four steps that are triggered by the external heat delivered by a heated substrate to the glycine loaded droplets. First, the droplet diameter is rapidly shrunk to approximately 50%, and then a localized nucleation is produced, followed by a fast radial growth from the nucleus to the droplet boundary, and finally, aging of the spherical agglomerates (FIG. 19B). The spherical crystal agglomerates were characterized using two methods: optical microscopy and scanning electron microscopy using a Quanta 3D Feg system. This method allows for the production of monodisperse glycine crystal agglomerates and offers an excellent method to control the rapid crystal growth, since the crystal formation is confined within the droplet.

Other embodiments are within the scope of the following claims.

What is claimed is:

1. A multi-layer microfluidic device for parallelization of microfluidic systems comprising:
   plural layers arranged in top of each other; and
   a distribution network including a plurality of channels to control the flow of a fluid, the plural layers including first and second generator layers, made of plates or substrates, each of the first and second generator layer having a fractal pattern of fluid channels aligned between the layers by through-holes formed in each layer, the plural layers further including (1) a dispersed phase distribution layer and (2) a continuous phase distribution layer, each of the dispersed phase distribution layer and the continuous phase distribution layer having a fractal pattern of fluid channels, wherein the dispersed phase distribution layer receives a first fluid and allows the first fluid to flow through its fractal pattern of fluid channels, the continuous phase distribution layer receives a second fluid, different from the first fluid, and allows the second fluid to flow through its fractal pattern of fluid channels, the first and second fluids flow separately through the through-holes to the first generator layer and mix up and form an emulsion in the first generator layer and the emulsion flows through the fractal pattern of fluid channels of the first generator layer until arriving at an outlet, and the first and second fluids flow separately through the through-holes to the second generator layer and mix up and form another emulsion in the second generator layer and the another emulsion flows through the fractal pattern of fluid channels of the second generator layer until arriving at the outlet.

2. The multi-layer microfluidic device of claim 1, wherein the device comprises inputs that are accessible from a surface of the device.

3. The multi-layer microfluidic device of claim 1, wherein the channels are on a substrate or plate made of polymeric plastic material such as poly(methyl-methacrylate), stainless steel, silicon, ceramics, or glass or a combination thereof.

4. The multi-layer microfluidic device of claim 1, wherein the channels are in a pattern based on any number that follows the equation $p \times m \times 2^n$, where p is an integer representing the number of petals, m is an integer representing the number of identical generation layers and n is an integer representing the number of levels of the fractal branching.

5. The multi-layer microfluidic device of claim 1, further comprising at least one inlet or input and at least 1 outlet or output to allow accessibility of immiscible liquids and exit of droplets.

6. A method of forming an emulsion comprising:
inputting a first fluid at a dispersed phase distribution layer, which has a first fractal pattern of fluid channels, the first fluid flowing from an input to multiple ends of the first fractal pattern of fluid channels;
inputting a second fluid at a continuous phase distribution layer, which has a second fractal pattern of fluid channels, the second fluid flowing from another input to multiple ends of the second fractal pattern of fluid channels;
passing the first and second fluids through a multi-layer device comprising, in addition to the dispersed phase distribution layer and the continuous phase distribution layer, at least first and second generator layers,
wherein the first and second generator layers are connected by through-holes, and
wherein each of the first and second generator layer includes a corresponding fractal pattern;
mixing the first and second fluids to form the emulsion, in the first and second generator layers; and
controlling the flow of the emulsion, through the fractal pattern of fluid channels of the first and second generator layers, to an outlet that dispenses the emulsion.

7. The method of claim 6, wherein the emulsion is monodisperse.

8. The method of claim 6, wherein the emulsion is polydisperse.

9. The method of claim 6, further comprising:
supplying a fluid to a processing zone having a curved surface such that the fluid forms a layer free of side edges.

10. The method of claim 9, wherein the processing zone includes a tube having a curved surface.

11. The method of claim 9, further comprising aligning an emulsion output around a tube having a curved surface.

12. The method of claim 9, further comprising thermally treating on the curved surface to form crystals and other monodisperse particles.

13. The method of claim 9, further comprising UV treating on the curved surface to form crystals and other monodisperse particles.

14. The method of claim 9, wherein the processing zone includes an open rounded surface.

15. The method of claim 6, wherein each channel is connected to a sensor, wherein the sensor detects a change of a function of the channel and signals to shut down a malfunctioning channel.

* * * * *